US010184150B2

(12) United States Patent
Hamamah et al.

(10) Patent No.: US 10,184,150 B2
(45) Date of Patent: Jan. 22, 2019

(54) FREE NUCLEIC ACIDS AND MIRNA AS NON-INVASIVE METHOD FOR DETERMINING EMBRYO QUALITY

(71) Applicants: INSERM (INSTITUT NATIONAL DE LA SANTÉ ET DE LA RECHERCHE MÉDICALE), Paris (FR); UNIVERSITE DE MONTPELLIER, Montpellier (FR); CENTRE HOSPITALIER UNIVERSITAIRE DE MONTPELLIER, Montpellier (FR)

(72) Inventors: Samir Hamamah, Montpellier (FR); Elodie Scalici, Montpellier (FR); Sabine Traver, Montpellier (FR)

(73) Assignees: INSERM (INSTITUT NATIONAL DE LA SANTÉ ET DE LA RECHERCHE MÉDICALE), Paris (FR); UNIVERSITÉ DE MONTPELLIER, Montpellier (FR); CENTRE HOSPITALIER UNIVERSITAIRE DE MONTPELLIER, Montpellier (FR)

( * ) Notice: Subject to any disclaimer, the term of this patent is extended or adjusted under 35 U.S.C. 154(b) by 15 days.

(21) Appl. No.: 15/321,213

(22) PCT Filed: Jun. 26, 2015

(86) PCT No.: PCT/EP2015/064534
§ 371 (c)(1),
(2) Date: Dec. 22, 2016

(87) PCT Pub. No.: WO2015/197824
PCT Pub. Date: Dec. 30, 2015

(65) Prior Publication Data

US 2017/0152557 A1 Jun. 1, 2017

(30) Foreign Application Priority Data

Jun. 27, 2014 (EP) .................................... 14306040

(51) Int. Cl.

| | |
|---|---|
| ***C12Q 1/68*** | (2018.01) |
| ***C12Q 1/6876*** | (2018.01) |
| ***C12Q 1/6883*** | (2018.01) |
| *C07H 21/02* | (2006.01) |
| *C07H 21/04* | (2006.01) |

(52) U.S. Cl.
CPC ......... *C12Q 1/6876* (2013.01); *C12Q 1/6883* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2013/0316360 A1* 11/2013 Hamamah ............ C12Q 1/6881 435/6.12

FOREIGN PATENT DOCUMENTS

| | | | |
|---|---|---|---|
| EP | 1 944 611 | A1 | 2/2014 |
| WO | 2012/069613 | A1 | 5/2012 |
| WO | 2014/020564 | A1 | 2/2014 |

OTHER PUBLICATIONS

Dimopoulou et al., "Follicular Fluid Oocyte/Cumulus-Free DNA Concentrations as a Potential Biomolecular Marker of Embryo Quality and IVF Outcome", Biomed Research International, Jun. 15, 2014, pp. 1659-1665, vol. 61, No. 4.

Czamanski-Cohen et al., "Increased plasma cell-free DNA is associated with low pregnancy rates among women undergoing IVF-embryo transfer" Reproductive Biomedicine Online, Jan. 1, 2013, pp. 36-41, vol. 26, No. 1.

Czamanski-Cohen et al., "Decrease in cell free DNA levels following participation in stress reduction techniques among women undergoing infertility treatment", Archives of Women's Mental Health, Jan. 14, 2014, pp. 251-253, vol. 17, No. 3.

Sang et al., "Identification of MicroRNAs in Human Follicular Fluid: Characterization of MicroRNAs That Govern Steroidogenesis in Vitro and Are Associated With Polycystic Ovary Syndrome", Journal of Endocrinology & Metabolism, Jul. 1, 2013, pp. 3068-3079, vol. 98, No. 7.

Roth et al., "Altered microRNA and gene expression in the follicular fluid of women with polycystic ovary syndrome", Journal of Assisted Reproduction and Genetics, Jan. 4, 2014, pp. 355-362, vol. 31, No. 3.

Yang et al., "Differentially expressed plasma microRNAs in premature ovarian failure patients and the potential regulatory function of mir-23a in granulosa cell apoptosis", Reproduction, May 31, 2012, pp. 235-244, vol. 144, No. 2.

Santonocito et al., "Molecular characterization of exosomes and their microRNA cargo in human follicular fluid: bioinformatic analysis reveals that exosomal microRNAs control pathways involved in follicular maturation", Fertility and Sterility, Dec. 1, 2014, pp. 1751-1761, vol. 102, No. 6.

Scalici et al., "Cell-free DNA in human follicular fluid as a biomarker of embryo quality", Human Reproduction, Sep. 29, 2014, pp. 2661-2669, vol. 29, No. 12.

Traver et al., "Cell-free nucleic acids as non-invasive biomarkers of gynecological cancers, ovarian, endometrial and obstetric disorders and fetal aneuploidy", Human Reproductive Update, Nov. 1, 2014, pp. 905-923, vol. 20, No. 6.

* cited by examiner

*Primary Examiner* — Sean McGarry
(74) *Attorney, Agent, or Firm* — W & C IP

(57) ABSTRACT

The present invention relates generally to the fields of reproductive medicine. More specifically, the present invention relates to in vitro non-invasive methods for determining the quality of an embryo by determining the level of the cell free nucleic acids or miR-29a or let7-b in the nucleic acid extract from a follicular fluid sample.

7 Claims, 10 Drawing Sheets

Figure 1:
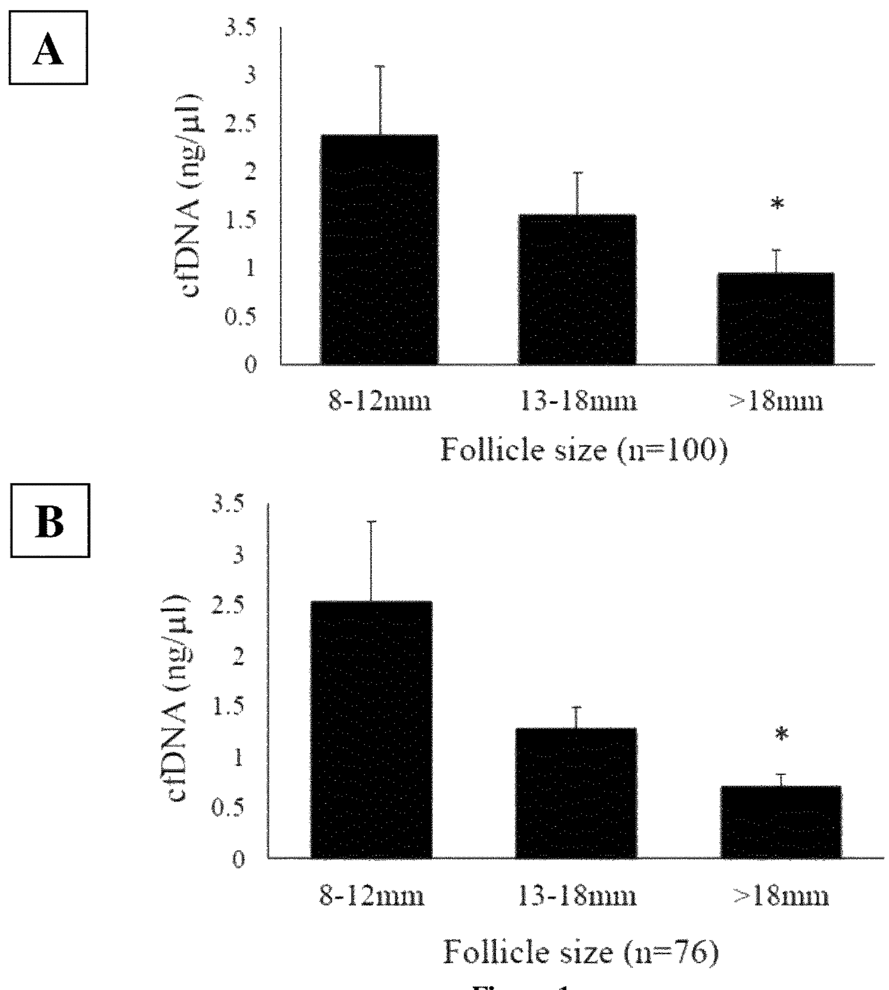

FREE NUCLEIC ACIDS AND MIRNA AS NON-INVASIVE METHOD FOR DETERMINING EMBRYO QUALITY

FIELD OF THE INVENTION

The present invention relates generally to the fields of reproductive medicine. More specifically, the present invention relates to methods and kits for determining the quality of an embryo.

BACKGROUND OF THE INVENTION

Currently, selection of the embryos with the highest implantation potential during assisted reproductive technology (ART) procedures relies only on morphological criteria. A new method based on time-lapse imaging has been recently described for the acquisition of embryo morphokinetic data to help such selection (Meseguer et al., 2011; Herrero and Meseguer, 2013). Nevertheless, the subjective observation of embryo morphology to predict a successful pregnancy shows limitations (Guerif et al., 2007; Assou et al., 2008; Aydiner et al., 2010; Assou et al., 2010). Therefore, many recent works have focused on the identification of new non-invasive biomarkers based on the analysis of the oocyte microenvironment to improve the accuracy of embryo selection (Pearson, 2006; Assou et al., 2008; van Montfoort et al., 2008; Assou et al., 2010; Aydiner et al., 2010; Uyar et al., 2013). In some studies, follicular fluid (FF) components, which are derived from plasma or secreted from granulosa cells, were investigated as potential biomarkers (De Placido et al., 2006; Baka and Malamitsi-Puchner, 2006; Yanaihara et al., 2007; Estes et al., 2009; Revelli et al., 2009; Borowiecka et al., 2012; Lédée et al., 2013). Indeed, FF, which surrounds the oocyte, is involved in follicular maturation, oocyte growth and the gradual acquisition of developmental competence. Consequently, FF might represent a reliable source of oocyte and embryo outcome biomarkers that could be used as supplemental prognostic/diagnostic tools in ART (Mermillod et al., 1999; Mendoza et al., 2002; Sutton et al., 2003; Krisher, 2004; Angelucci et al., 2006; Baka and Malamitsi-Puchner, 2006).

Cell-free DNA (cfDNA) fragments can be detected in the bloodstream (Mandel and Métais, 1948; Swarup and Rajeswari, 2007) and result from apoptotic or necrotic processes. They are released via a passive or an active mechanism (Jahr et al., 2001; Stroun et al., 2001). Nuclear and mitochondrial DNA can be released passively in the blood from apoptotic or necrotic cells (Schwarzenbach et al., 2011) and are then phagocytized by macrophages in healthy individuals, in whom the basal cfDNA level remains low (Jiang et al., 106 2003; Pisetsky and Fairhurst, 2007). CfDNA can also be actively secreted by cells (Gahan et al., 2008), leading to an increase of cfDNA circulating level in some cancers and other serious disorders. For that reason, cfDNA is used as non-invasive diagnostic and/or prognostic biomarker for some cancers and other severe pathologies (Paci et al., 2009; Vlassov et al., 2010; Gao et al., 2010; Kamat et al., 2010; Schwarzenbach et al., 2011; Gahan, 2012; Chen et al., 2013; da Silva Filho et al., 2013). Similarly, the emergence of non-invasive prenatal testing, based on foetal cfDNA detection in the maternal blood, constitutes a promising approach in obstetrics and gynaecology (Wright and Burton, 2009, Liao et al., 2014). So far, no study has evaluated cfDNA content in ovarian follicles, although follicular atresia is the result of many apoptotic events in granulosa cells.

In the present invention, the inventors asked whether cfDNA could be detected in FF and whether its quantification could be used to develop an innovative prognostic test for embryo quality. To this aim, the inventors quantified cfDNA in the FF of individual pre-ovulatory follicles from patients undergoing conventional in vitro fertilization (IVF) or intracytoplasmic sperm injection (ICSI). The inventors then explored whether cfDNA level and integrity were related to the follicle size and hormonal content, the patients' clinical characteristics and IVF outcomes. The inventors demonstrate that cfDNA quantification in FF represent an innovative and non-invasive biomarker to improve embryo selection in IVF procedures.

SUMMARY OF THE INVENTION

The present invention relates generally to the fields of reproductive medicine. More specifically, the present invention relates to in vitro non invasive methods and kits for determining the quality of an embryo by determining the level of the cell free nucleic acids in the nucleic acid extraction.

DETAILED DESCRIPTION OF THE INVENTION

The inventors studied cell-free DNA (cfDNA) quantification in individual human follicular fluid (FF) samples as a new non-invasive predictive biomarker for in vitro fertilization (IVF) outcomes. Hundred individual FF samples from 43 female patients undergoing conventional IVF (n=26) or Intracytoplasmic Sperm Injection (ICSI) (n=17) were collected and their cfDNA level quantified. Follicle size was calculated based on the FF volume. Each corresponding cumulus oocyte-complex was isolated for IVF or ICSI procedures.

Human FF samples from individual pre-ovulatory follicles contain measurable amounts of cfDNA. CfDNA level was significantly higher in small follicles than in large ones. Moreover, cfDNA concentration was significantly and negatively correlated with follicle size. A significant negative correlation between DNA integrity and 17β-estradiol level in FF samples at oocyte collection day was observed. CfDNA level in FF samples corresponding to top quality embryos was significantly lower than in FF samples related to poor quality embryos. Similarly, cfDNA level was also significantly lower in FF samples related to embryos with low fragmentation rate than with high fragmentation rate. After adjustment for confounding variables, the odds to obtain a top quality embryo reached 82%, if the cfDNA level in the corresponding FF samples was <4.79 ng/μl.

The inventors demonstrated that CfDNA level in human FF samples was significantly correlated with embryo quality and present an innovative non-invasive biomarker to improve IVF outcomes.

The inventors also demonstrated that miRNA levels in human FF samples was significantly correlated with embryo quality and present an innovative non-invasive biomarker to improve IVF outcomes. The inventors found a significant and negative correlation between FF let-7b expression level and blastulation rate and embryo developmental potential. Indeed, low FF let-7b expression was significantly associated with the probability to obtain a blastocyst. In addition, FF miR-29a levels predicted significantly the clinical pregnancy outcome.

Accordingly, the present invention relates to an in vitro non invasive method for determining the quality of an embryo comprising the steps consisting of i) providing a biological sample, ii) extracting the cell free nucleic acids from the biological sample and iii) determining the level of the cell free nucleic acids in the nucleic acid extraction.

In some embodiments, the present invention relates to an in vitro non invasive method for determining the quality of an embryo comprising the steps consisting of i) providing an individual follicular fluid sample, ii) extracting the cell free nucleic acids from the follicular fluid sample and iii) determining the level of the cell free nucleic acids in the nucleic acid extraction.

The term "biological sample" refers to an individual follicular fluid, follicular fluid sample from individual preovulatory follicles, blood, serum, plasma.

As used herein the term "embryo" has its general meaning in the art and refers to a fertilized oocyte or zygote. The term "embryo" also refers to cells in all stages of development from a fertilized oocyte or zygote up to the 5 or 6 days (blastocyst stage). Said fertilization may intervene under a classical in vitro fertilization (cIVF) conditions or under an intracytoplasmic sperm injection (ICSI) procedure. Examples of embryos that may be assessed by the methods of the invention include 1-cell embryos (also referred to as zygotes), 2-cells embryo, 3-cells embryo, 4-cells embryo, 5-cells embryo, 6-cells embryo, 8-cells embryo, etc. typically up to and including 16-cells embryo, any of which may be derived by any convenient manner, e.g. from an oocyte that has matured in vivo or from an oocyte that has matured in vitro. As used herein, the term "blastocyst" refers to the structure formed in the early embryogenesis of mammals, after the formation of the morula. It possesses an inner cell mass (ICM), or embryoblast, which subsequently forms the embryo, and an outer layer of cells, or trophoblast, which later forms the placenta. The trophoblast surrounds the inner cell mass and a fluid-filled blastocyst cavity known as the blastocoele. The human blastocyst comprises 70-100 cells. Blastocyst formation begins at day 5/6 after fertilization in humans.

According to the invention, the oocyte may result from a natural cycle, a modified natural cycle or a stimulated cycle for cIVF or ICSI. The term "natural cycle" refers to the natural cycle by which the female or woman produces an oocyte. The term "modified natural cycle" refers to the process by which, the female or woman produces an oocyte or two under a mild ovarian stimulation with GnRH antagonists associated with recombinant FSH or hMG. The term "stimulated cycle" refers to the process by which a female or a woman produces one or more oocytes under stimulation with GnRH agonists or antagonists associated with recombinant FSH or hMG.

The term "classical in vitro fertilization" or "cIVF" refers to a process by which oocytes are fertilised by sperm outside of the body, in vitro. IVF is a major treatment in infertility when in vivo conception has failed. The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm, and occasionally as a method of in vitro fertilization, especially that associated with sperm donation.

By "determining the quality of an embryo" it is meant that the method of the invention aims at determining whether an embryo is competent in the context of in vitro fertilization. The method of the invention allows the assessment of the ability of an embryo to perform successfully either or both in terms of conferring a high pregnancy rate and/or resulting in a healthy person. Accordingly the method of the invention allows selection of the best embryo with low fragmentation rate that is able to give rise to pregnancy.

The term "competent embryo" refers to an embryo with a high implantation rate leading to pregnancy. The term "high implantation rate" means the potential of the embryo when transferred in uterus, to be implanted in the uterine environment and to give rise to a viable fetus, which in turn develops into a viable offspring absent of a procedure or event that terminates said pregnancy.

The method of the invention is applicable preferably to women but may be applicable to other mammals (e.g., primates, dogs, cats, pigs, cows, mouse . . . ).

As used herein the term "nucleic acid" has its general meaning in the art and refers to refers to a coding or non coding nucleic sequence. Nucleic acids include DNA (deoxyribonucleic acid) and RNA (ribonucleic acid). Example of nucleic acid thus include but are not limited to DNA, mRNA, tRNA, rRNA, tmRNA, miRNA, piRNA, snoRNA, and snRNA. According to the invention, the term "nucleic acid" refers to nucleic acids present in the follicular fluid sample. The term "nucleic acid" also relates to nucleic acids originate from oocyte or ovarian follicle that might go into follicular fluid and/or the blood circulation.

Any methods well known in the art may be used by the skilled artisan in the art for extracting the cell free nucleic acid from the prepared sample. For example, the method described in the example may be used.

In a particular embodiment the method of the invention comprises the steps consisting of i) determining the level of the cell free nucleic acid in the nucleic acid extraction, ii) comparing the level determined at step i) with a reference value, and iii) concluding that the embryo is competent when the level determined at step i) is lower than the reference value.

In a particular embodiment, the reference value is a threshold value or a cut-off value that can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the nucleic acid levels (obtained according to the method of the invention) with a defined threshold value. In one embodiment of the present invention, the threshold value is derived from the nucleic acid levels (or ratio, or score) determined in a follicular fluid derived from one or more patients undergoing IVF or ISCI. Furthermore, retrospective measurement of the nucleic acid levels (or ratio, or scores) in properly banked historical follicular fluid of patients undergoing IVF or ISCI may be used in establishing these threshold values.

In a particular embodiment, the reference value is 4.79 ng/μl.

Determination of the level of the nucleic acid can be performed by a variety of techniques well known in the art. In a particular embodiment, quantitative PCR may be performed for determining the level of DNA such as described in El Messaoudi et al., 2013; Mouliere et al., 2013; Thierry et al., 2013; Umetani et al., 2006 and WO2012/028746. In particular, the determination of the level of the nucleic acid may be performed by ALU-qPCR and techniques described in the examples.

In a further aspect of the present invention, the levels of miRNA are measured.

As used herein, the term "miR" has its general meaning in the art and refers to the miRNA sequence publicly available from the data base http://microma.sanger.ac.uk/sequences/.

Accordingly, the present invention also relates to an in vitro non invasive method for determining the quality of an embryo comprising the steps consisting of i) providing a biological sample, ii) extracting the cell free nucleic acids and miRNAs from the biological sample and iii) determining the level of the cell free nucleic acids and/or at least one miRNA selected from the group consisting of let7-b and miR-29a in the nucleic acid extraction.

In some embodiments, the present invention relates to an in vitro non invasive method for determining the quality of an embryo comprising the steps consisting of i) providing an individual follicular fluid sample, ii) extracting the cell free nucleic acids and miRNAs from the follicular fluid sample and iii) determining the level of the cell free nucleic acids and/or at least one miRNA selected from the group consisting of let7-b and miR-29a in the nucleic acid extraction.

A further aspect of the invention relates to an in vitro non invasive method for determining the quality of an embryo, comprising a step of determining in the nucleic acid extraction the level of cell free nucleic acids and let7-b.

A further aspect of the invention relates to an in vitro non invasive method for determining the quality of an embryo, comprising a step of determining in the nucleic acid extraction the level of cell free nucleic acids and miR-29a.

A further aspect of the invention relates to an in vitro non invasive method for determining the quality of an embryo, comprising a step of determining in the nucleic acid extraction the level of let7-b and miR-29a.

A further aspect of the invention relates to an in vitro non invasive method for determining the quality of an embryo, comprising a step of determining in the nucleic acid extraction the level of cell free nucleic acids, let7-b and miR-29a.

The method of the invention may further comprise a step consisting of comparing the expression level of at least one miRNA in the nucleic acid extraction with a reference value, wherein detecting differential in the expression level of the miRNA between the nucleic acid extraction and the reference value is indicative of embryo quality.

In one embodiment, the reference value may correspond to the expression level determined in a biological sample such as follicular fluid associated with a competent embryo. Accordingly, a higher or equal expression level of miR-29a and lower or equal expression level of let7-b than the reference value is indicative of a competent embryo, and lower expression level of miR-29a and higher expression level of let7-b than the reference value is indicative of a non-competent embryo.

In one embodiment, the reference value may correspond to the expression level determined in a biological sample such as follicular fluid associated with a non-competent embryo. Accordingly, a higher expression level of miR-29a and lower expression level of let7-b than the reference value is indicative of a competent embryo, and lower or equal expression level of miR-29a and higher or equal expression level of let7-b than the reference value is indicative of a non-competent embryo.

The method of the invention is particularly suitable for reaching a clinical decision. As used herein the term "clinical decision" refers to any decision to take or not take an action that has an outcome that affects the health or survival of the embryo. In particular, in the context of the invention, a clinical decision refers to a decision to implant or not the embryo of in the uterus of the patient. In particular the method as above described will thus help embryologist to avoid the transfer in uterus of embryos with a poor potential for pregnancy outcome. The method as above described is also particularly suitable for improving in vitro fertilization outcomes and avoiding multiple pregnancies by selecting the competent embryo able to lead to an implantation and a pregnancy and therefore fewer embryos could be transferred at each cycle, resulting in a decreased incidence of multiple pregnancies.

In a further aspect, the invention relates to a method for enhancing the pregnancy outcome of a patient comprising the steps consisting of i) providing a plurality of embryos, ii) determining the quality of the embryo by the method according to the invention, iii) selecting the most competent embryo, and iv) implanting the embryo selected at step iii) in the uterus of said patient.

A method of implanting a competent embryo in a patient undergoing in vitro fertilization, comprising the steps of:

a) collecting oocytes from said patient;

b) generating embryos from said oocytes by fertilizing said oocytes in vitro;

c) determining the quality of the embryo by performing the method according to the invention;

and d) implanting said embryo having a higher probability of being competent in said patient.

The invention also relates to a kit for performing the methods as above described, wherein said kit comprises means for determining the level of the cell free nucleic acid. Typically, the kits include primers, probes, macroarrays or microarrays. The kit may further comprise hybridization reagents or other suitably packaged reagents and materials needed for the particular hybridization protocol, including solid-phase matrices, if applicable, and standards. Alternatively the kit of the invention may comprise amplification primers that may be pre-labelled or may contain an affinity purification or attachment moiety. The kit may further comprise amplification reagents and also other suitably packaged reagents and materials needed for the particular amplification protocol.

The invention will be further illustrated by the following figures and examples. However, these examples and figures should not be interpreted in any way as limiting the scope of the present invention.

FIGURES

FIG. 1: Comparison of follicular fluid cell-free DNA levels in the three follicle size groups. A, all individual follicles were included (n=100) (*p=0.024). B, Only individual follicles containing an oocyte were included (n=76) (*p=0.007).

Figure 2:
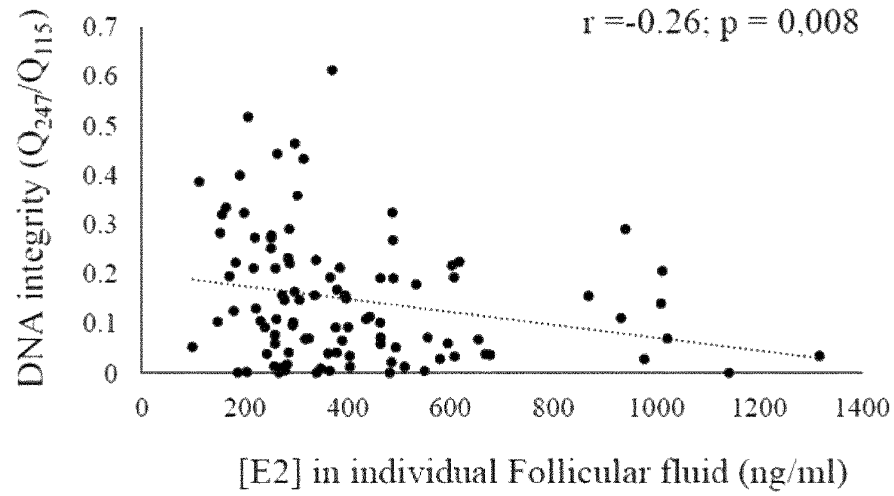

FIG. 2: Linear correlation between DNA integrity and E2 concentration in individual follicular fluid samples (r=−0.26; p=0.008).

Figure 3:
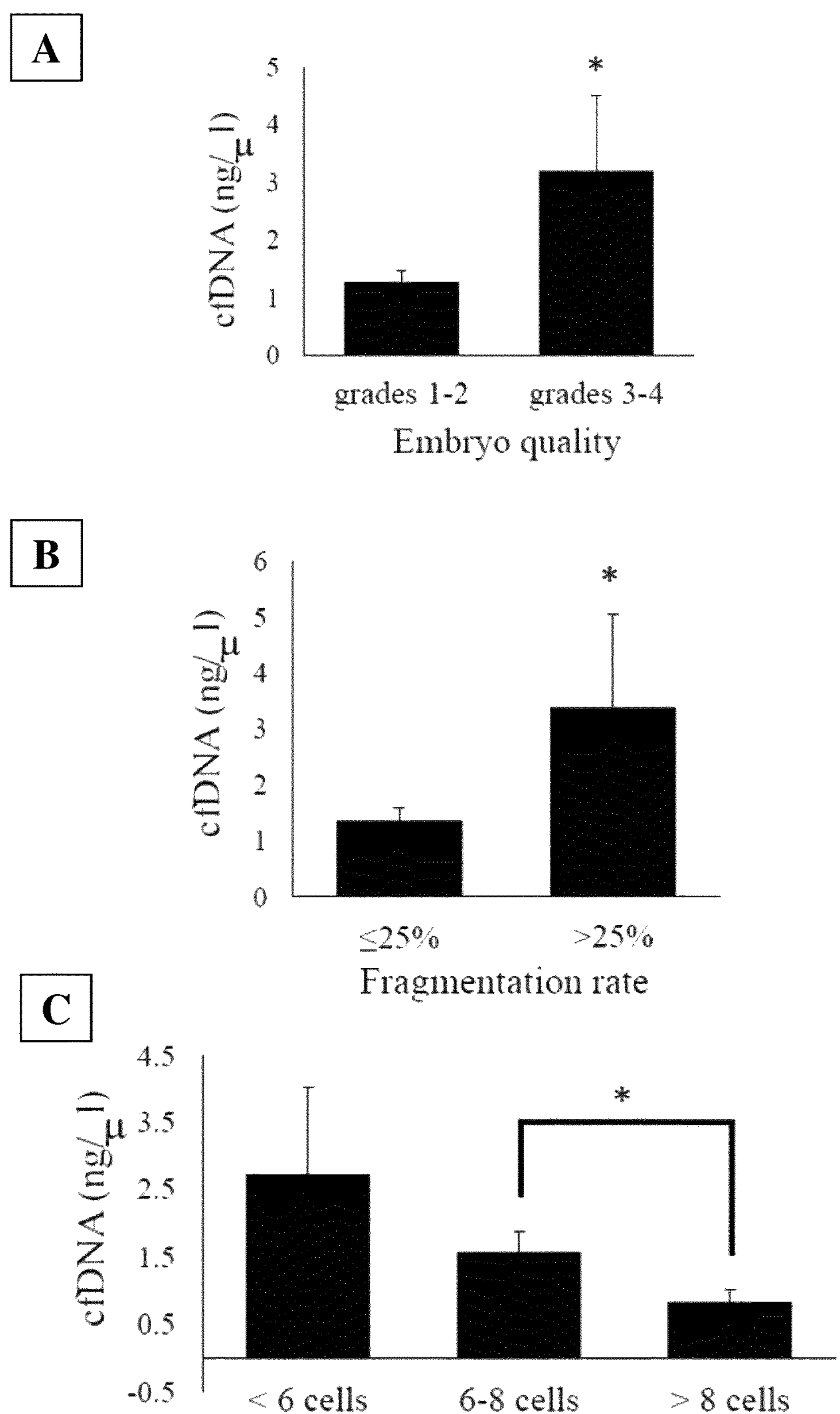

FIG. 3: A, Cell-free DNA content in follicular fluid samples grouped according to the quality at day 3 of the embryo derived from the corresponding oocyte (grade 1-2 versus grade 3-4, *p=0.02). B, Cell-free DNA in follicular fluid samples grouped according to fragmentation rate at day 3 (≤25% versus >25%, *p=0.02) in the embryo derived from the corresponding oocyte. C, Cell-free DNA content in follicular fluid samples grouped according to blastomere number at day 3 (<6, 6-8 or >8 cells) in the embryo derived from the corresponding oocyte. The comparison between the 6-8 and the >8 cell groups is significant (*p=0.04).

Figure 4:
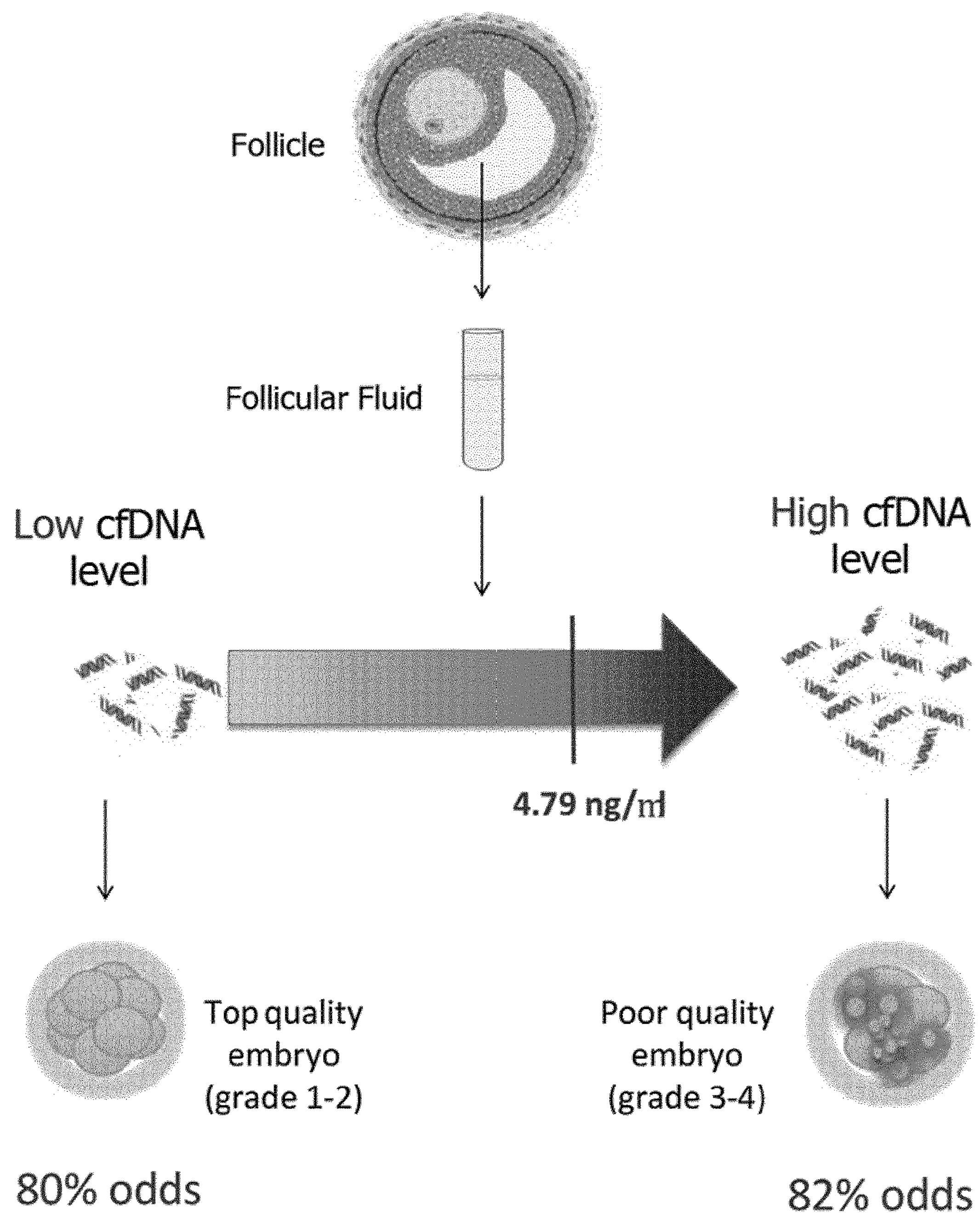

FIG. 4: Working model showing that the odds of obtaining a top quality embryo are 82% if the corresponding follicular fluid contained less than 4.79 ng/μl of cell-free DNA. Conversely, the odds of obtaining a poor quality embryo are 80% if the corresponding follicular fluid contained more than 4.79 ng/μl of cell-free DNA.

Figure 5:
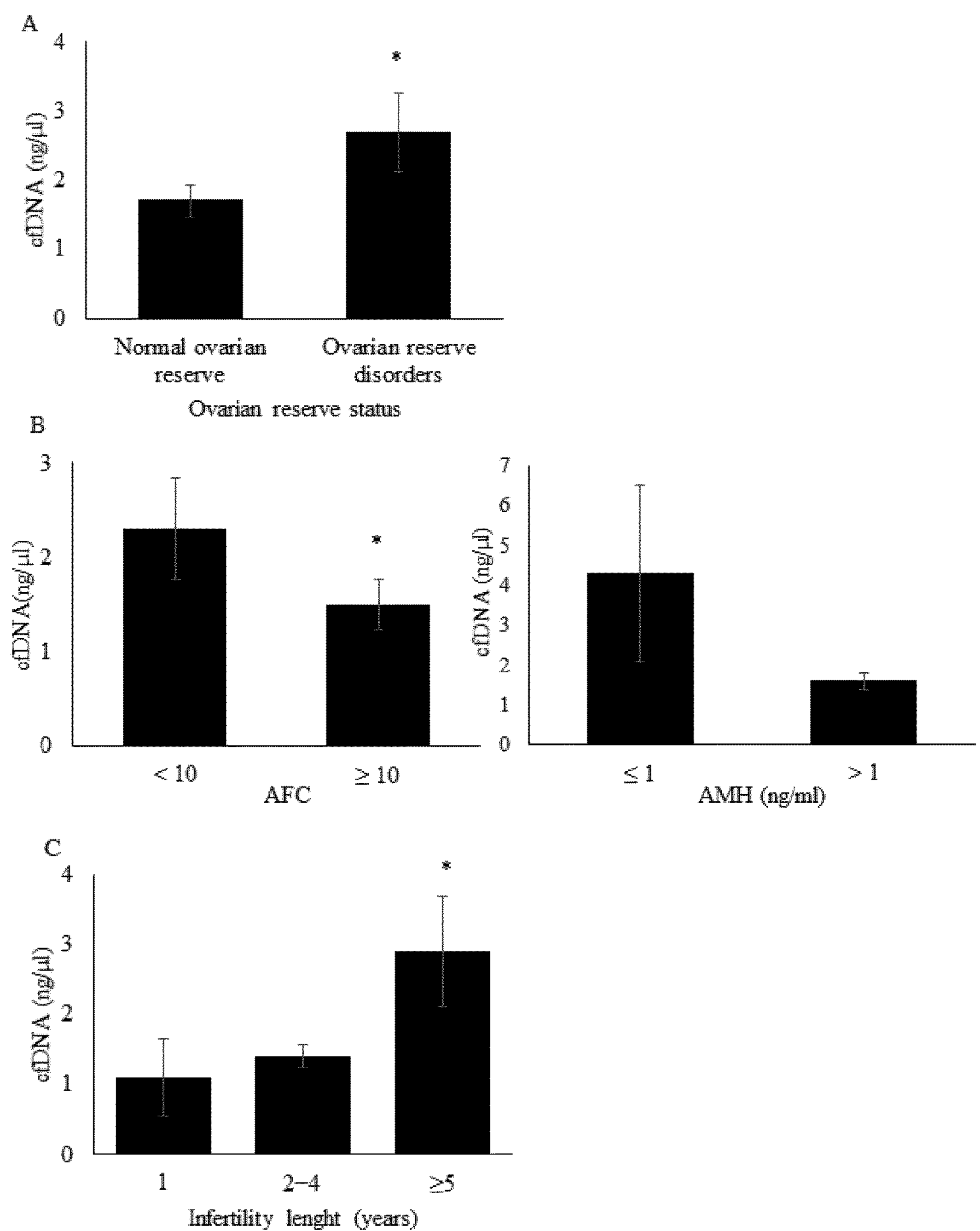

FIG. 5: Cell-free DNA level in follicular fluid (FF) pools according to the patients' ovarian reserve status, ovarian reserve parameters and infertility length. A, FF intra-follicular cfDNA content in patients with normal ovarian reserve versus patients with ovarian reserve disorders (ovarian insufficiency and polycystic ovary syndrome); *p=0.03. B, FF cfDNA content according to the ovarian reserve parameters; left panel: AFC (<10 versus ≥10, *p=0.04); right panel: AMH (≤1 versus >1 ng/ml, *p=0.06). C, FF cfDNA levels according to the infertility length (1 versus ≥5 years, *p=0.049).

Figure 6:
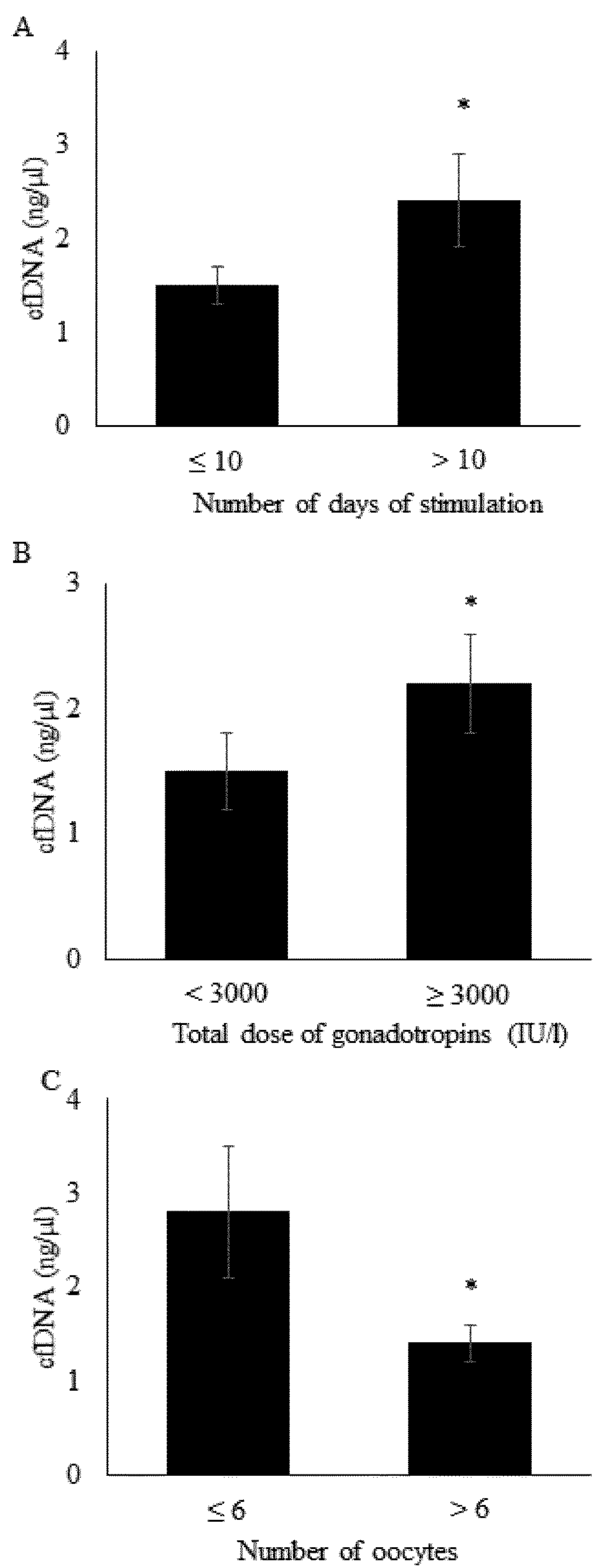

FIG. 6: CfDNA level in follicular fluid pools according to the ovarian stimulation protocol and ovarian response. A, FF cfDNA content according to the length of ovarian stimulation (≤10 versus >10 days), *p=0.008. B, FF cfDNA content according to the total dose of gonadotropins (<3000 versus ≥3000 IU/l, *p=0.01). C, FF cfDNA content according to the number of retrieved oocytes (≤6 versus >6 oocytes, *p=0.045).

Figure 7:
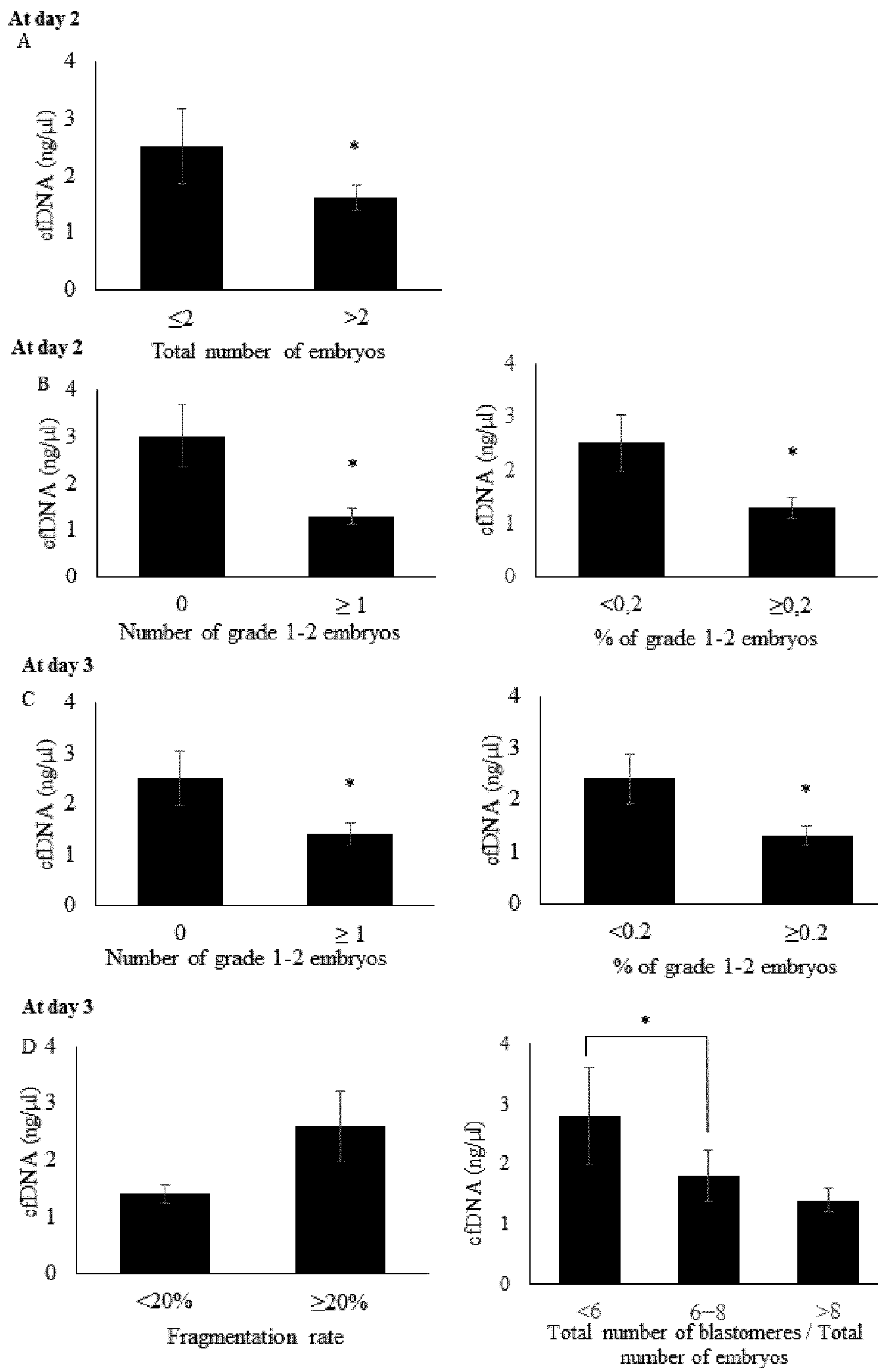

FIG. 7: CfDNA level in follicular fluid pools according to the embryo outcome at day 2 and 3. A, FF cfDNA content according to the total number of embryos at day 2 (≤2 versus >2, *p=0.03). B, FF cfDNA content according to, left panel: the number of top quality (grade 1-2) embryos per patient (0 versus ≥1, *p=0.002) at day 2, right panel: ratio between number of top quality embryos and total number of embryos (<0.2 versus ≥0.2, *p=0.04) at day 2. C, FF cfDNA content according to, left panel: number of top quality (grade 1-2) embryos per patient (0 versus ≥1, *p=0.006) at day 3, right panel: ratio between number of top quality embryo and total number of embryos (<0.2 versus ≥0.2, *p=0.02) at day 3. D, FF cfDNA content according to, left panel: fragmentation rate at day 3 (<20% versus ≥20%, p=0.18) and right panel: ratio between blastomere number and total embryo number at day 3 (<6 versus 6-8, *p=0.02).

Figure 8:
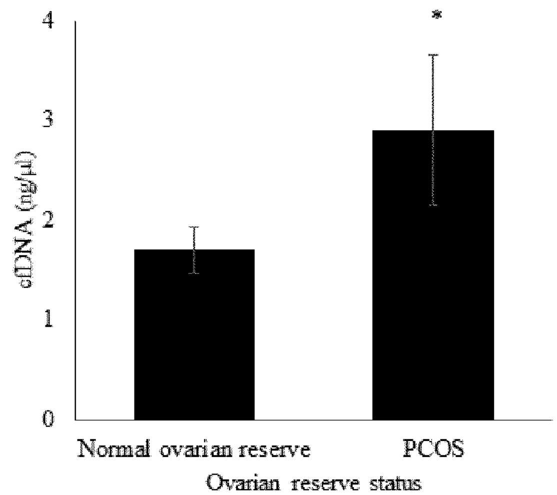

FIG. 8: Comparison of cfDNA levels in follicular fluid pools of patients with normal ovarian reserve (n=94) and patients with polycystic ovary syndrome (PCOS) (n=17); *p=0.049.

Figure 9:
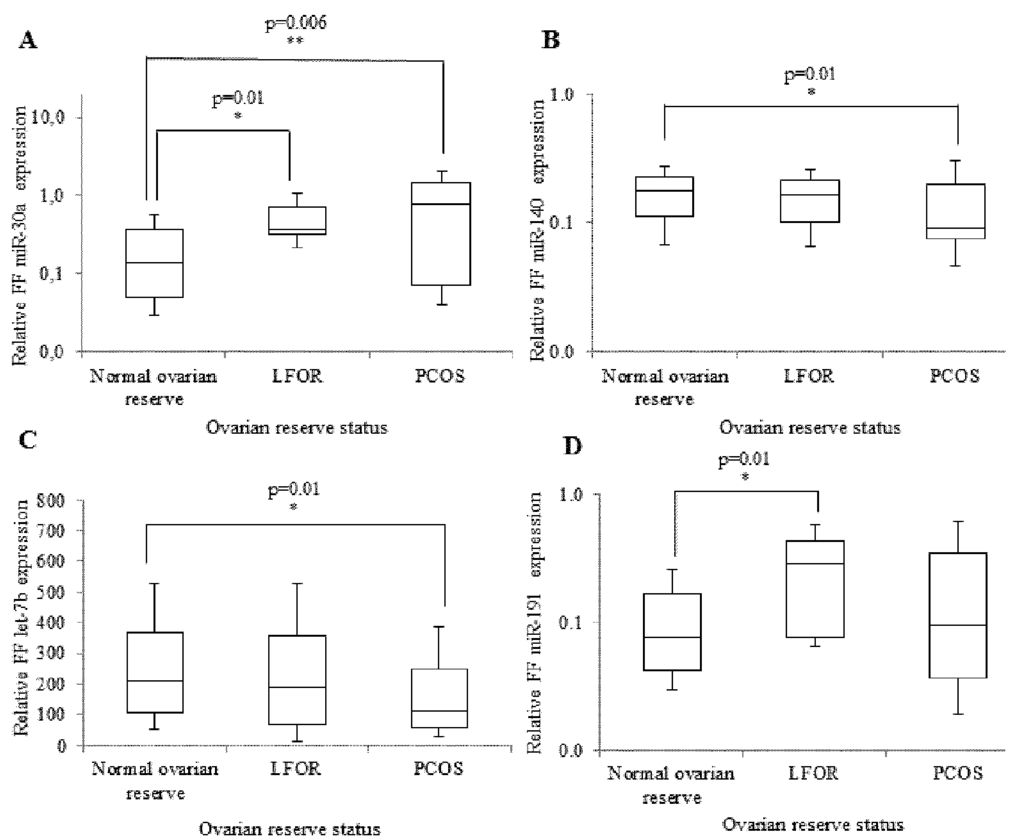

FIG. 9: Comparison of the relative miRNA expression in follicular fluid (FF) pools from women with different ovarian reserve status (normal ovarian reserve, polycystic ovary syndrome (PCOS) and low function ovarian reserve (LFOR)). A, FF miR-30a; B, FF miR-140; C, FF let-7b; D, FF miR-191.

Figure 10:
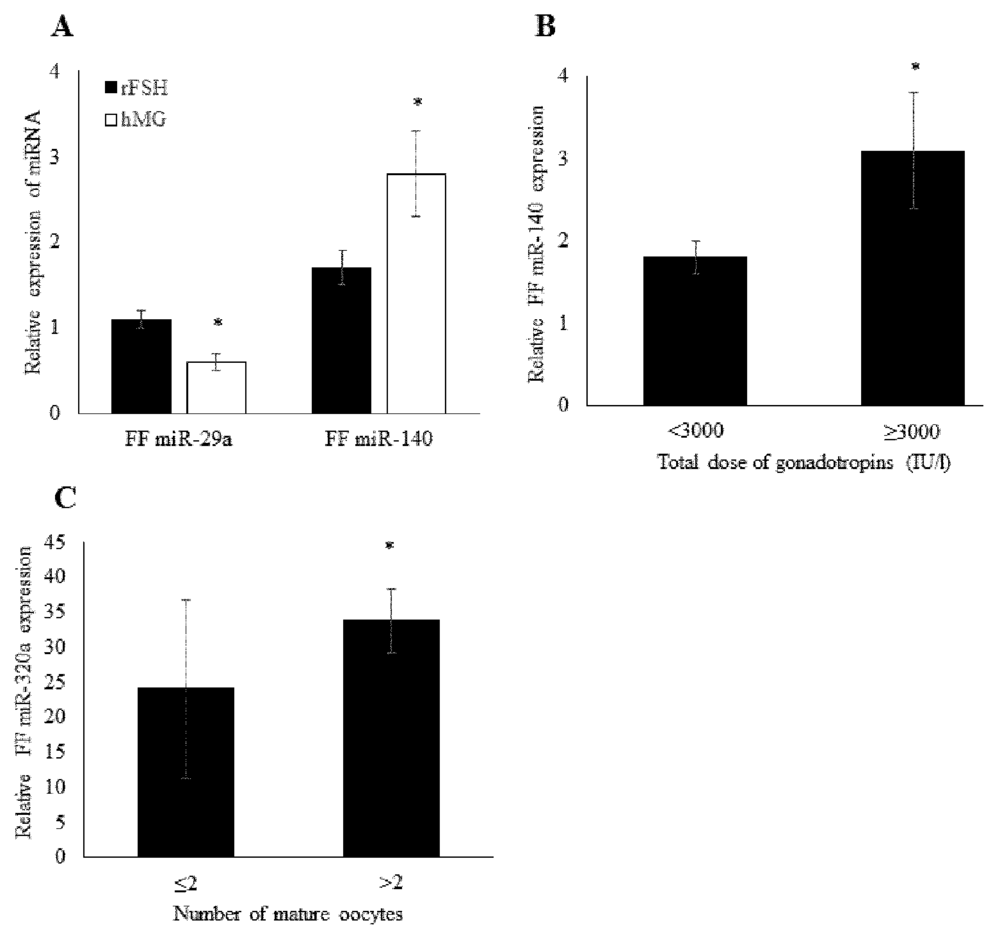

FIG. 10: A, Comparison of FF miR-29a and miR-140 expression level relative to the type of treatment (highly purified human menopausal gonadotropin, hMG, versus recombinant follicle-stimulating hormone, r-FSH). B, Differential FF miR-140 expression according to the total dose of gonadotropins (<3000 versus ≥3000 IU/l). C, Comparison of FF miR-320a expression level relative to the number of retrieved mature oocytes (≤2 versus >2 mature oocytes).

Figure 11:
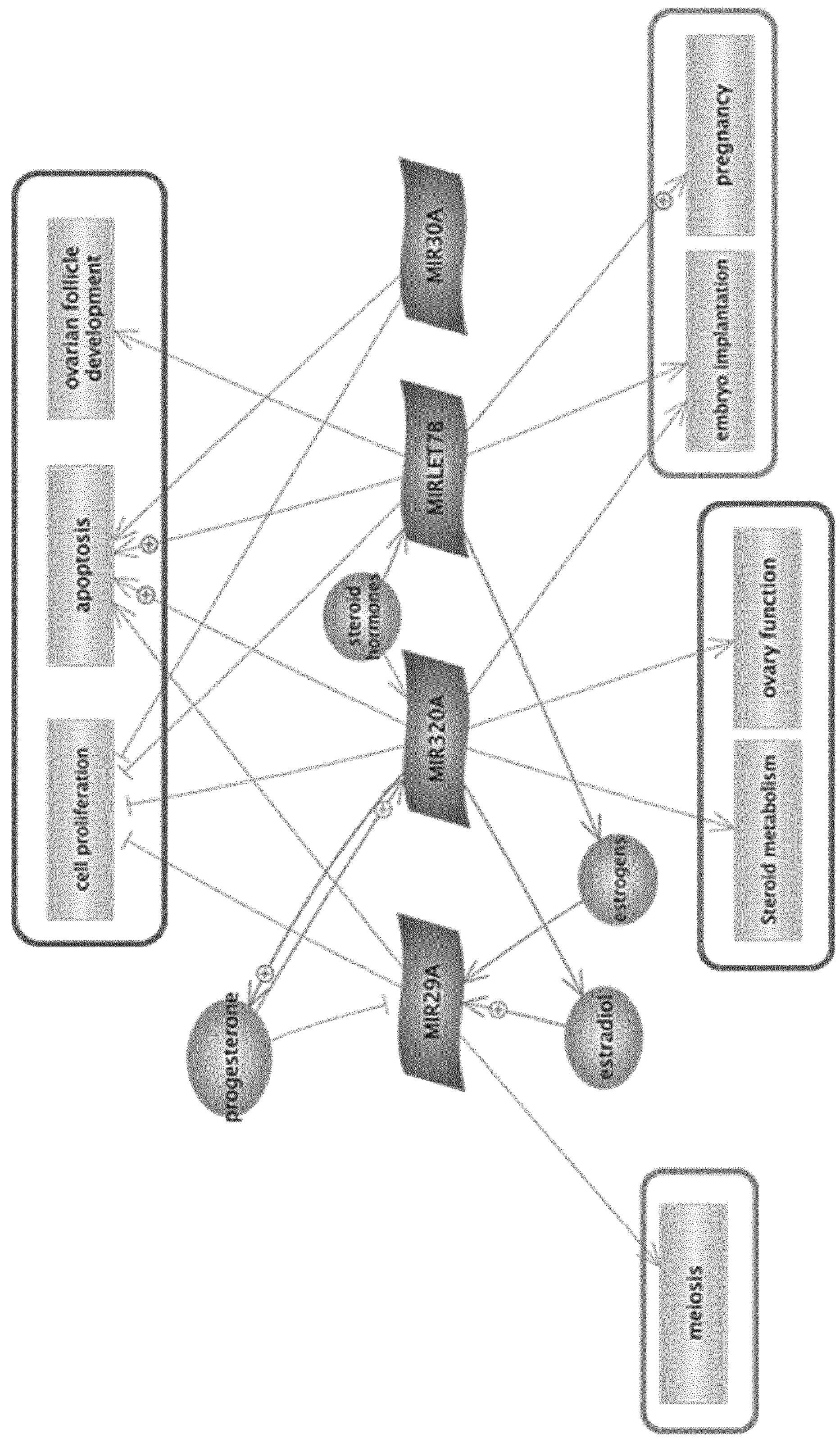

FIG. 11: Pathways involved in reproductive processes and including the circulating miRNAs miR-29a, miR-320a, let-7b and miR-30a, and their interaction with steroid hormones.

Figure 12:
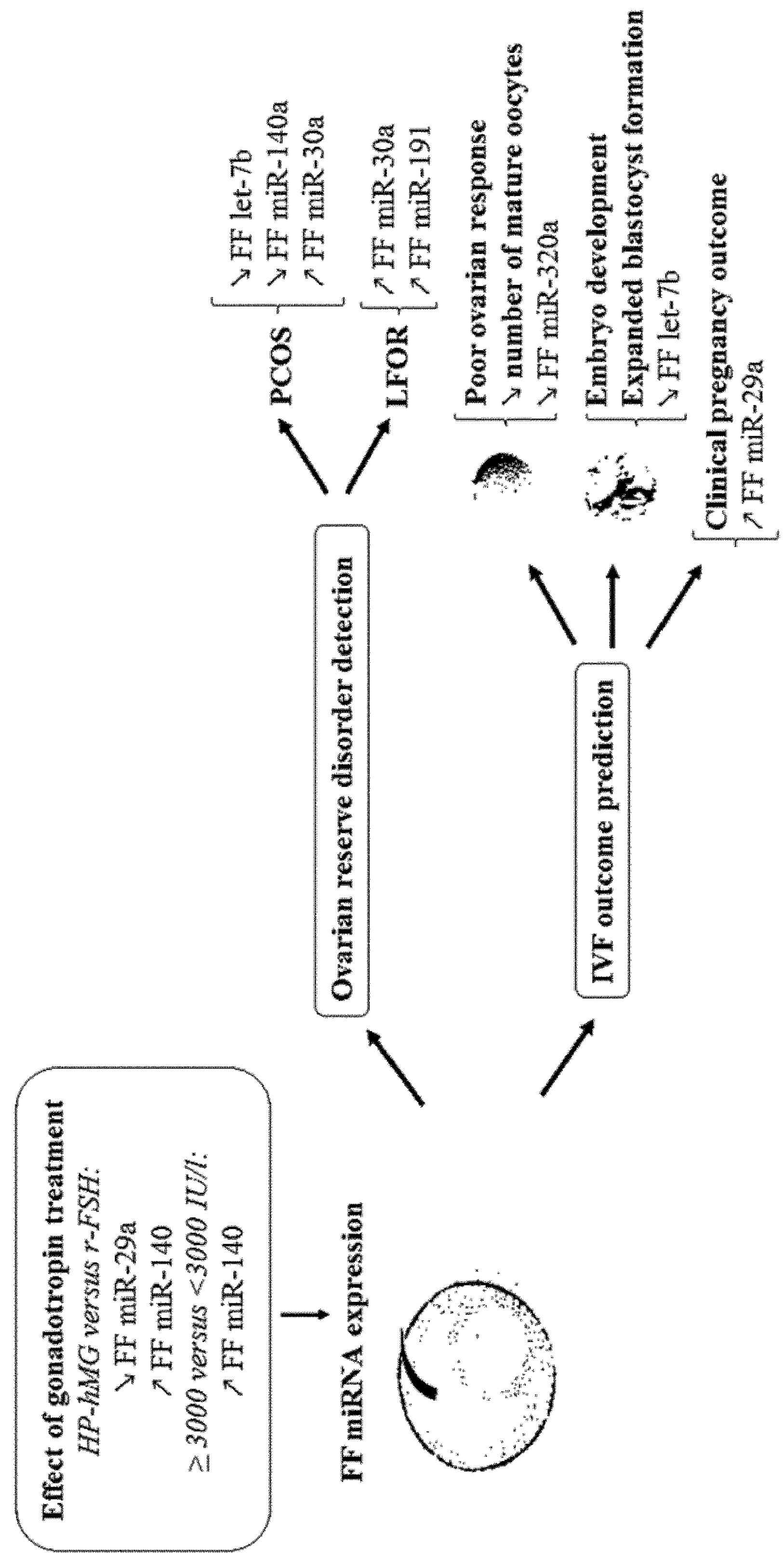

FIG. 12: Schematic model showing that miRNA expression profiling in FF samples provides powerful tools for ovarian reserve disorder detection and IVF outcome prediction during IVF. The expression of some FF miRNAs varies according to the gonadotropin treatment. HPhMG, highly purified human menopausal gonadotropin; r-FSH, follicle-stimulating hormone; PCOS, polycystic ovary syndrome; LFOR, low function ovarian reserve.

EXAMPLES

Example 1

Material & Methods

Patients' Characteristics

This prospective study included 43 women undergoing controlled ovarian stimulation and IVF (n=26) or ICSI (n=17) procedures at the ART-PGD Department of the CHU of Montpellier, France. Written informed consent was obtained for the use of FF samples at the time of oocyte collection and the local Institutional Review Board approved the study. Based on the Rotterdam criteria, patients with polycystic ovary syndrome were excluded (Rotterdam, 2004). The patients' characteristics are reported in Table I. The women's age ranged from 24 to 40 years (mean±SD: 33.3±4.5 years) and their body mass index (BMI) was between 18 and 31 kg/m$^2$ (mean±SD: 22.2±3.1 kg/m2). Infertility duration was 3.9±3.1 years (mean±SD) and 77% of couples were considered to have primary infertility.

Female infertility was the cause of the consultation in 58% of couples, while male factors, mixed or unexplained infertility were found in 32%, 5% and 5% of couples, respectively. The ovarian reserve (based on the anti-Müllerian hormone level and antral follicle count) was normal in 91% of women, except for four patients with ovarian insufficiency. The baseline hormonal status was evaluated in each patient at day 3 of the cycle (Table I).

In Vitro Fertilization and Follicular Fluid Sample Collection

Thirty-seven of the 43 patients received a long GnRH agonist treatment (Decapeptyl; IpsenPharma) and the other six patients a short one. In both cases, it was followed by ovarian stimulation with recombinant FSH (Puregon, MSD). The ovarian response was monitored by measuring serum 17β-estradiol (E2) concentration and by transvaginal ultrasound evaluation of follicular and endometrial growth.

When at least three follicles had reached a diameter of 17 mm or more, ovulation was induced by a single injection of 250 μg of human chorionic gonadotropin (Ovitrelle; Merck Serono). Oocyte retrieval was performed by transvaginal ultrasound-guided aspiration 36 hours after the injection and each pre-ovulatory follicle was aspirated individually without flushing.

Individual FF samples were collected and the corresponding cumulus-oocyte complexes were isolated for conventional IVF or ICSI procedures. Before microinjection for ICSI, oocyte maturity was assessed after denudation. Oocytes were individually cultured in a 30 μl microdroplet of culture medium (Vitrolife) under oil at 37° C. in 6% $CO_2$ and humid atmosphere. Normal fertilization was confirmed by the presence of two pronuclei and two polar bodies 18 to 20 hours after microinjection or insemination. Early cleavage was observed at 25 or 27 hours after microinjection or insemination, respectively. Three days after oocyte retrieval, embryo quality was graded from 1 to 4, according to the following morphological criteria: (a) number of blastomeres, (b) blastomere regularity and (c) fragmentation rate (Table II). An embryo was considered of top quality (grade 1 and 2) if 6 to 8 blastomeres of regular size with less than 25% fragmentation were observed. Top quality embryos were transferred or frozen at day 3, whereas grade 3 and 4 embryos were discarded.

Follicular Fluid Preparation

To avoid any blood contamination, only clear FF samples were included, whereas bloodstained and cloudy FF samples were excluded. In total 100 FF samples were used for this work. The volume of each FF sample was measured and the diameter of the corresponding follicle was calculated based on the FF volume and on the assumption that follicles are spherical. Thus, pre-ovulatory follicles were classified in three groups: small (8-12 mm in diameter; n=22), intermediate (13-18 mm in diameter; n=59) and large (>18 mm in diameter; n=19) (Table I, in bold). FF samples were centrifuged at 3000 g for 15 min to eliminate cell debris and supernatants were immediately stored at −80° C.

Determination of E2 Concentration in Follicular Fluid Samples

E2 concentration in FF samples was measured by immuno-chemiluminescence using commercial kits (Cobas e411; Roche Diagnostics).

Cell-Free DNA Extraction and Quantification by ALU-qPCR

FF samples were prepared as described by Umetani et al., 2006. Briefly, 20 μl of each FF sample was mixed with 20 μl of a buffer containing 25 ml/l Tween 20, 50 mmol/l Tris and 1 mmol/l EDTA and then digested with 16 μg of proteinase K (PK) (Qiagen) at 50° C. for 20 minutes followed by heat-inactivation and insolubilisation at 95° C. for 5 min. Samples were then centrifuged at 10,000 g for 5 min and supernatants collected and stored at −80° C. until cfDNA quantification.

CfDNA was quantified by qPCR for human ALU repeats using two primer sets that generate a 115-bp amplicon (ALU115 primers) and a 247-bp amplicon (ALU247 primers), respectively (Umetani et al., 2006). For each ALU-qPCR, 1 μl of each PK-digested FF sample was added to a reaction mixture (final volume: 10 μl) containing 0.25 μM of forward and reverse primers (ALU115 or ALU247) and 5 μl of 2× LightCycler®480 SYBR Green I master mix (Roche Applied Science, Germany). FF cfDNA concentrations were calculated based on a standard curve prepared with successive dilutions of genomic DNA (Umetani et al., 2006). A negative control (without template) was added in each qPCR plate. All measures were performed in quadruplicate.

DNA Integrity

DNA released from necrotic cells varies in size, whereas DNA released from apoptotic cells is uniformly truncated in shorter fragments of 185 to 200 bp (Giacona et al., 1998). DNA integrity was thus calculated as the $Q_{247}/Q_{115}$ ratio, where $Q_{247}$ corresponds to the cfDNA level obtained using the ALU 247 primers and $Q_{115}$ to the concentration obtained with the ALU 115 primers. As the ALU 115 primer annealing sites are within the ALU 247 primer annealing sites, the qPCR ratio would be equal to 1, if cfDNA fragments were generated only by necrosis and to 0 if they were produced only by apoptosis.

Statistical Analysis

Univariate analysis was performed for each variable. Continuous parametric data are presented as mean±standard deviation (SD), and categorical variables as numbers and percentages. We used the $\chi 2$ test for categorical variables and the Mann-Whitney or Student's t test for quantitative variables, according to the normality of the distribution, assessed with the Shapiro-Wilk test. A multivariate analysis was carried out using a logistic regression model in which we included all variables associated with a p value lower than 0.20 in the univariate analysis. Then, a stepwise procedure allowed obtaining the final multivariate model. As one patient could be evaluated several times (repeated measures), a linear mixedeffects model for repeated measures, allowing taking into account repeated measures as random variables was used. Regression coefficients with confidence intervals (CI) to 95% are given. The ability of cfDNA level to predict a top quality embryo was determined by constructing the Receiver Operating Characteristic (ROC) curve and calculating the area under the curve (AUC) with CI to 95%. We calculated the sensitivity, specificity, negative and positive predictive values, for the optimal cut-off. Statistical tests were performed using the R (version 2.15.2) software. Results were considered significant when p≤0.05.

Results

Follicular Fluid Cell-Free DNA Level in Relation to Follicle Size

Quantification by ALU 115-qPCR of total cfDNA in 100 individual human FF samples from pre-ovulatory follicles showed that its concentration varied from 0.11 to 15.73 ng/μl (mean±SD: 1.62±2.08 ng/μl; median: 1.01 ng/μl). CfDNA level in FF samples was not significantly associated with the patients' clinical characteristics (Table I). Moreover, cfDNA levels in small follicles (8-12 mm in diameter) were significantly higher than in large follicles (>18 mm) (2.38±0.72 ng/μl vs 0.95±0.24 ng/μl, respectively, p=0.024) (FIG. 1A). This finding was confirmed, even when only follicles containing an oocyte (n=76) were considered (2.54±0.78 ng/μl vs 0.71±0.44 ng/μl, respectively, p=0.007) (FIG. 1B). Likewise, the correlation coefficient showed that FF cfDNA concentration was significantly and negatively correlated with follicle size (r=−0.24; p=0.017) and this linear correlation was stronger in follicles containing an oocyte (r=−0.34; p=0.003). The mean FF cfDNA concentration per follicle in younger (<37 years, n=31) and older (≥37 years, n=12) patients was 1.68±2.25 ng/μl and 1.42±1.42 ng/μl, respectively. CfDNA levels and age were not correlated linearly. After adjusting for the women's age in a statistical linear mixed model, cfDNA levels remained significantly associated with follicle size (β=−0.15; p=0.022).

DNA Integrity and E2 Level in Follicular Fluid

In our individual human FF samples, the mean $Q_{247}/Q_{115}$ ratio was 0.15 (SD: 0.13) with a range from 0 to 0.61, suggesting that cfDNA originated mainly from apoptosis. DNA integrity and follicle size were not significantly correlated. By contrast, a strong significant and negative correlation between DNA integrity and intra-follicular E2 level (409.6±238.4 ng/ml) was found (r=−0.26; p=0.008) (FIG. 2), suggesting more necrosis in follicles with low E2 level.

Cell-Free DNA Concentration in Human Individual Follicular Fluid Samples and IVF Outcomes There was no significant difference between cfDNA concentration, measured by ALU115 qPCR, in FF samples from follicles with and without oocyte (empty zona pellucida) (Table III). Among the 26 oocytes isolated from patients undergoing ICSI, 21 had reached meiotic maturity (i.e., were in metaphase II) and the other five oocytes were blocked in metaphase I (Table III). Therefore, the oocyte maturity rate before ICSI was about 81% [95% CI (65.695.9)]. CfDNA concentration was not significantly different in the FF samples related to mature and normally fertilized oocytes or immature oocytes and non-fertilized oocytes, respectively (Table III). IVF or ICSI cycles resulted in 59 zygotes with two pronuclei from 69 oocytes (86% of fertilization).

Among the 49 embryos obtained, 37 were considered as top quality embryos (grades 1 and 2) [75.5%, 95% CI (63.5-87.5)] and early cleavage was observed in 13 of the 49 embryos [26.5%, 95% CI (14.1-38.9)]. CfDNA level was significantly higher in FF samples related to oocytes that generated poor quality embryos (grades 3 and 4) compared to FF samples related to top embryos (grades 1 and 2) (3.2±1.3 ng/μl vs 1.27±0.21 ng/μl, respectively, p=0.02) (FIG. 3A and Table III). In agreement with this observation, cfDNA level was significantly lower in FF samples related to embryos with low fragmentation rate (≤25%) than with high fragmentation rate (>25%) (1.37±0.23 ng/μl vs 3.38±1.67 ng/μl, respectively, p=0.02) (FIG. 3B and Table III). Moreover, cfDNA concentration tended to be higher in FF samples corresponding to embryos with fewer blastomeres (<6 cells at day 3), suggesting that development was more often delayed in embryos derived from oocytes that matured in a cfDNA-rich follicular environment (FIG. 3C and Table III).

Predictive Value of Cell-Free DNA Level for Embryo Quality

ROC analysis showed that a total cfDNA level (ALU115 qPCR) lower than 4.79 ng/μl in a FF sample was significantly associated with elevated odds that the corresponding oocyte would produce a top quality embryo (grades 1 and 2) [Crude Odd Ratio (COR): 18 (1.8-183.2); p=0.015] (Table IV). After adjustment for several patients' characteristics such as age, BMI, type of infertility (primary versus secondary) and follicle size, a low FF cfDNA level remained independently and significantly associated with higher odds of obtaining a top quality embryo [Adjusted Odd Ratio (AOR): 19.5 (1.3-303.6); p=0.034] (Table IV). In addition, the area under the ROC curve (Table IV) that analyses the prediction potential of FF cfDNA concentration to obtain a top quality embryo was 0.58 (0.36-0.8). The sensitivity of FF cfDNA level for embryo quality prediction was very high (97%) as well as the positive (82%) and negative predictive value (80%) (Table IV and FIG. 4).

Discussion

This study demonstrates for the first time the presence of cfDNA in human FF samples from individual pre-ovulatory follicles of patients undergoing IVF. It also shows that cfDNA level in individual FF samples is negatively correlated with follicle size and associated with embryo quality. Our data suggest that a FF cfDNA concentration threshold of 4.79 ng/μl could be used to predict embryo quality at day 3; specifically, an oocyte isolated from a follicle with FF cfDNA values lower than this threshold, has 82% chance to produce a top quality embryo.

As FF is derived both from serum and granulosa cell secretions (Rodgers and Irving-Rodgers, 2010), we decided to use ALU-qPCR, a method initially developed for measuring cfDNA in serum (Umetani et al., 2006), to quantify cfDNA in FF samples. This approach allowed the reliable detection and quantification of cfDNA in FF samples and it was highly sensitive and easy to perform. Quantitative PCR with the ALU 115 primers quantifies the total cfDNA, whereas qPCR with the ALU247 primers amplifies only large fragments, coming from necrosis rather than apoptosis. Consequently, the $Q_{247}/Q_{115}$ ratio represents the proportion of cfDNA generated by necrosis, and thus, the integrity of cfDNA. We found a strong significant and negative correlation between DNA integrity and intra-follicular E2 level, suggesting that reduced E2 production could be associated with necrotic events in pre-ovulatory follicles. This observation is in agreement with studies proposing a role for tumour necrosis factoralpha (TNFα, factor promoting necrosis), in the regulation of steroidogenesis in ovarian follicles, particularly, by decreasing E2 level in the follicle (Best et al., 1994; Montgomery Rice et al., 1998).

CfDNA amount in FF samples was significantly and negatively correlated with follicle size, suggesting an association with the functional and dynamic state of pre-ovulatory follicles. Indeed, in mammals, including humans, FF composition changes according to the follicle size (Wen et al., 2006; Nandi et al., 2007; Malizia et al., 2010; Nishigaki et al., 2011). Moreover, the apoptotic rate is more elevated in porcine and bovine granulosa cells from small antral follicles than from medium and large follicles (Yang and Rajamahendran, 2000; Lin and Rui, 2010). Consequently, high cfDNA levels in small follicles could be explained by an increase of apoptotic events in these follicles compared to healthy pre-ovulatory large follicles. Furthermore, the mean FF DNA integrity was 0.15 in our cohort, suggesting that about 85% of FF cfDNA was of apoptotic origin. Therefore, cfDNA in FF samples should be mainly the consequence of apoptotic events in the follicle and FF cfDNA level and origin might thus reflect follicle health and maturity.

FF composition strongly influences oocyte quality, its developmental competence and the quality of the subsequent embryo (Mermillod et al., 1999, Mendoza et al., 2002; Sutton et al., 2003; Baka and Malamitsi-Puchner, 2006). For this reason, many studies highlighted FF as an important source of potential non-invasive biomarkers for oocyte and embryo quality prediction (De Placido et al., 2006; Baka and Malamitsi-Puchner, 2006; Yanaihara et al., 2007; Estes et al., 2009; Revelli et al., 2009; Borowiecka et al., 2012; Lédée et al., 2013). We observed that cfDNA level in FF samples was strongly and significantly associated with embryo quality at day 3. Indeed, the FF of oocytes that produced top quality embryos and embryos with low fragmentation rate (≤25%) contained significantly less cfDNA than the FF of oocytes that generated poor-quality embryos and embryos with high fragmentation rate (>25%). Furthermore, slow-dividing embryos were related to follicles with high FF cfDNA level. These observations suggest that oocytes that develop in a cfDNA-rich environment: (i) could have accumulated "negative signals" with potential harmful consequences on embryo health and development, or (ii) lack certain "positive signals" normally transmitted by healthy granulosa cells. These "abnormal signals" do not seem to disturb oocyte maturation and fertilization, because these two processes occurred normally even in a cfDNA-rich environment. However, they might affect at least two of the three criteria for embryo quality (listed in Table II): the early embryo cleavage and the fragmentation rate. Indeed, the majority of embryos showing delayed development (<6 blastomeres at day 3) and high fragmentation rates (>25%) came from follicles with high FF cfDNA levels. In agreement with these results, it was reported that in the well-in-drop oocyte/embryo in vitro culture system, elevated apoptosis in granulosa cells and small follicle size impaired oocyte developmental competence and thus goat and cow embryo health (Han et al., 2006; Feng et al., 2007). Moreover, a recent study found a significant association between the DNA profile of spent embryo culture medium and embryo fragmentation rate (Stigliani et al., 2013). Indeed, they detected mitochondrial and genomic DNA in spent embryo culture medium and found that the mitochondrial cfDNA concentration was higher in medium samples in which embryos with bad quality cleavage were cultured compared to spent medium from top grade embryos.

The presence of high cfDNA concentrations in FF or in spent culture medium could be the consequence but also one of the causes of poor embryo quality. If we hypothesize that FF cfDNA is toxic for oocytes and transmit “negative signals” that could further affect embryo development, then its presence in FF will harm the oocyte and consequently the embryo. CfDNA could also be only a consequence of elevated apoptosis of granulosa cells that cannot establish the dialog with the oocyte and supply all the elements needed for its normal development. Alternatively, oocytes could lack “positive signals” from the surrounding cells and also suffer from high cfDNA level toxicity. In any case, cfDNA quantification in FF samples could represent an innovative non-invasive approach for embryo selection in addition to the currently used morphological criteria. We thus evaluated the predictive potential of cfDNA FF levels for embryo quality evaluation. We found that the odds to obtain a top quality embryo were 82% when FF cfDNA concentration was <4.79 ng/μl and the odds to obtain a poor quality embryo were 80% when cfDNA concentration was ≥4.79 ng/μl.

As FF is the by-product of oocyte aspiration from ovarian follicles, its collection is noninvasive and cfDNA quantification is easy to perform. Therefore, the use of cfDNA as a predictive biomarker of embryo quality could represent an attractive way to develop new noninvasive prognostic tests for IVF. A larger study will be conducted to investigate the relationship between cfDNA level in FF samples and implantation rate, independently of embryo morphology.

The presence of embryotoxic factors in the serum of infertile patients with repeated spontaneous abortions (Ecker et al., 1993; Sargent and Dokras, 1996) motivated investigations on circulating cfDNA quantification in the bloodstream for patients undergoing IVF procedures (Hart et al., 2005; Czamanski-Cohen et al., 2013; Czamanski-Cohen et al., 2014). Czamanski-Cohen et al., reported that increased plasma cfDNA was associated with low pregnancy rates in women undergoing IVF (Czamanski-Cohen et al., 2013). They suggested that this high circulating cfDNA level, probably due to maternal cell apoptotic events, could create a hostile environment for conception. As there is communication between FF and plasma because FF composition results from the combination of secretions from the granulosa cells and plasma components (Rodgers and Irving-Rodgers, 2010), it is conceivable that cfDNA from FF might go into the blood circulation and constitute a measurable biomarker of ovarian health and embryo outcome in plasma or serum samples during an IVF procedure. Furthermore, the same group showed that the stress caused by the IVF procedure was responsible for increasing cfDNA in patients’ blood and that relaxation techniques helped to significantly reduce cfDNA levels in blood and therefore improve the IVF outcome (Czamanski-Cohen et al., 2014). Taken together, our results and these previously published data suggest that cfDNA quantification in both FF and serum could give a better predictive picture of embryo quality, and could be used routinely in addition to the subjective morphological criteria. Moreover, if further studies will show that elevated cfDNA levels contribute to poor embryo quality, it could be possible to envisage a therapeutic approach based on DNase treatment to reduce cfDNA concentration in blood and/or in FF with the final aim of improving ART outcome.

TABLE I

Patients’ characteristics, hormonal treatment and follicular size classification and association with cell-free DNA levels in follicular fluid. β ± SE, regression coefficient ± standard error; SD, standard deviation; BMI, body mass index; FSH, follicle-stimulating hormone; LH, luteinizing hormone; E2, 17β-estradiol; AMH, anti-Mullerian hormone; AFC, antral follicle count; IVF, in vitro fertilization; ICSI, intracytoplasmic sperm injection.

| Variable | Mean | n (%) | Min-Max | SD | □ ± SE | p-value |
|---|---|---|---|---|---|---|
| Age (years) | 33.3 | — | 24-40 | 4.5 | 0.02 ± 0.05 | 0.69 |
| <37 years | — | 31 (72) | — | — | 0.29 ± 0.52 | 0.59 |
| ≥37 years | | | — | — | | |
| BMI (kg/m$^2$) | — | 12 (28) | 18-31 | 3.1 | −0.13 ± 0.09 | 0.15 |
| | | — | | | | |
| | 22.23.9 | — | | | | |
| Infertility lenght (years) | | | 1-10 | 2.3 | 0.02 ± 0.15 | 0.87 |
| Infertility aetiology (%) | | — | — | — | — | — |
| Male factor | — | 14 (32%) | — | — | — | — |
| Female factor | — | 25 (58%) | — | — | −0.22 ± 0.52 | 0.68 |
| Mixed infertility | — | 2 (5%) | — | — | −0.37 ± 1.01 | 0.72 |
| Unexplained infertility | — | 2 (5%) | — | — | 0.70 ± 1.1 | 0.53 |
| Primary infertility (%) | — | 33 (77) | — | — | −0.73 ± 0.56 | 0.19 |
| Secondary infertility (%) | — | 10 (23) | — | — | | |
| Cycle number | 1.3 | — | 1-4 | 0.7 | −0.22 ± 0.3 | 0.6 |
| Female baseline evaluation | | | | | | |
| FSH (IU/l) | 7.8 | — | 3.3-13.7 | 1.5 | −0.03 ± 0.11 | 0.8 |
| LH (IU/l) | 5.0 | — | 1.5-8.7 | 2.2 | 0.21 ± 0.14 | 0.13 |
| E2 (pg/ml) | 49.6 | — | 16.4-100.1 | 20.8 | −0.002 ± 0.01 | 0.88 |
| AMH (ng/ml) | 2.8 | — | 1-9.3 | 2.2 | 0.07 ± 0.14 | 0.64 |
| AFC | 13.1 | — | 5-26 | 5.4 | 0.01 ± 0.05 | 0.92 |
| Normal ovarian reserve (%) | — | 39 (91) | — | — | −0.26 ± 0.85 | 0.76 |
| Ovarian insufficiency (%) | — | 4 (9) | — | — | | |
| Long protocol | — | 37 (86) | — | — | −0.64 ± 0.83 | 0.44 |
| Short protocol | — | 6 (14) | — | — | | |

TABLE I-continued

Patients' characteristics, hormonal treatment and follicular size classification and association with cell-free DNA levels in follicular fluid. β ± SE, regression coefficient ± standard error; SD, standard deviation; BMI, body mass index; FSH, follicle-stimulating hormone; LH, luteinizing hormone; E2, 17β-estradiol; AMH, anti-Mullerian hormone; AFC, antral follicle count; IVF, in vitro fertilization; ICSI, intracytoplasmic sperm injection.

| Variable | Mean | n (%) | Min-Max | SD | □ ± SE | p-value |
|---|---|---|---|---|---|---|
| Ovarian response | | | | | | |
| Peak E2 level (pg/ml) | 1,512.4 | — | 494-3,620 | 740.9 | −0.01 ± 0.01 | 0.88 |
| FIV | — | 26 (60) | — | — | −0.01 ± 0.45 | 0.99 |
| ICSI | — | 17 (40) | — | — | | |
| **N° follicles 8 to ≤12 mm** | **0.5** | **22** | **0-4** | **1.0** | — | — |
| **N° follicles 13 to ≤18 mm** | **1.4** | **59** | **0-4** | **1.2** | — | — |
| **N° follicles >18 mm** | **0.4** | **19** | **0-2** | **0.7** | — | — |

TABLE II

Embryo quality classification at day 3. Embryo quality was graded from 1 to 4 (1-2: top quality embryos; 3-4: poor quality embryos) based on the following morphological criteria (i) number of blastomeres, (ii) blastomere regularity and (iii) fragmentation rate.

| Day 3 | grade 1 | grade 2 | grade 3 | | grade 4 |
|---|---|---|---|---|---|
| number of blastomeres | 6-8 cells | 6-8 cells | 6-8 cells | <6 cells or >8 cells | — |
| blastomeres regularity | regular | regular | irregular | regular or irregular | regular or irregular |
| Fragmentation rate | ≤10% | 10-25% | 26-40% | <40% | >40% |

TABLE III

Association between cell-free DNA levels in follicular fluid and IVF outcomes.

| FF associated with | n/number of FF analyzed (%) | cfDNA (ng/μl) Mean ± SD [95% CI] | β ± SE | p-value* |
|---|---|---|---|---|
| Empty zona pellucida | 24/100 (24) | 1.94 ± 0.39 [1.14; 2.74] | −0.5 ± 0.49 | p = 0.31 |
| Oocytes | 76/100 (76) | 1:52 ± 0.25 [1.03; 2.01] | | |
| Immature oocytes (MI) | 5/26 (19) | 0.93 ± 0.28 [0.15; 1.7] | 0.53 ± 0.96 | p = 0.52 |
| Mature oocytes (MII) | 21/26 (81) | 1.31 ± 0.28 [0.73; 1.9] | | |
| No normal fertilized oocyte | 10/69 (14) | 1.0 ± 0.21 [0.52; 1.48] | 0.58 ± 0.76 | p = 0.45 |
| Normal fertilized oocyte | 59/69 (86) | 1.67 ± 0.31 [1.05; 2.29] | | |
| No embryo | 51/100 (51) | 1.5 ± 0.21 [1.08; 1.92] | 0.15 ± 0.43 | p = 0.71 |
| Embryo | 49/100 (49) | 1.74 = 0.37 [1.0; 2.48] | | |
| No early cleavage | 36/49 (73) | 1.93 ± 0.48 [0.95; 2.92] | −0.67 ± 0.84 | p = 0.44 |
| Early cleavage | 13/49 (27) | 1.21 ± 0.3 [0.56; 1.85] | | |
| No Top embryo (grades 3 and 4) | 12/49 (24) | 3.2 ± 1.3 [0.33; 6.06] | 1.9 ± 0.81 | p = 0.02 |
| Top embryo (grades 1 and 2) | 37/49 (76) | 1.27 ± 0.21 [0.85; 1.69] | | |
| Fragmentation rate embryo (>25%) | 9/49 (18) | 3.38 ± 1.68 [0.48; 7.24] | 2.28 ± 0.91 | p = 0.02 |
| Fragmentation rate embryo (≤25%) | 40/49 (82) | 1.37 ± 0.23 [0.91; 1.84] | | |
| Embryo with <6 cells | 12/49 (24) | 2.73 ± 1.31 [0.15; 5.6] | −0.39 ± 0.23 | p = 0.11 |
| Embryo with 6-8 cells | 29/49 (60) | 1.58 ± 0.29 [0.99; 2.18] | | |
| Embryo with >8 cells | 8/49 (16) | 0.83 ± 0.18 [0.4; 1.26] | | |

β ± SE, regression coefficient ± standard error; FF, follicular fluid, MII, oocyte at metaphase II; MI, oocyte at metaphase I.

Oocyte maturity was assessed only for ICSI cycles (n = 26). The FF samples associated with the mature oocytes used for ICSI cycles and the oocytes used for IVF were included for fertilization assessment (n = 69).

*p-value is the result of linear mixed models.

TABLE IV

| Prediction of embryo quality using a cell-free DNA value threshold. | | | | |
|---|---|---|---|---|
| Probability to obtain a top quality embryo | | | | |
| cf-DNA (ng/μl) | Crudde OR [95% CI] | p-value | Adjusted OR [95% CI] | p-value |
| <4.79 vs ≥4.79 | 18 [1.8-183.2] | p = 0.015 | 19.5 [1.3-303.6] | p = 0.034* |
| Prediction of obtaining a top quality embryo for [cfDNA] threshold of 4.79 ng/μl | | | | |
| AuROC [95% CI] | Se (%) | Sp (%) | PPV (%) | NPV (%) |
| 0.58 [0.36-0.8] | 97 | 33 | 82 | 80 |

*Adjustment for age, BMI, type of infertility (primary versus secondary) and follicle size.
Se, sensitivity; Sp, specificity, PPV, positive predictive value; NPV, negative predictive value.

Example 2

Material & Methods

Patients

This prospective study recruited 100 women enrolled in conventional IVF (n=31) or ICSI (n=69) program at the ART-PGD Department of the University Hospital of Montpellier. The patients' characteristics are detailed in Table 1. The women's age was 34.3±4.5 years (mean±SD; range: 23 to 43 years) and the body index mass (BMI) was 23.3±4.2 kg/m$^2$ (mean±SD; range: 17 and 39 kg/m$^2$). The infertility length was 3.5±1.7 years (mean±SD). For 61% of the couples this was the first IVF or ICSI cycle and the remaining 39% of the couples had undergone at least one cycle (mean cycle number±SD: 2.1±1.3). In 11% of the couples, no specific cause of infertility was detected, while in the other couples, male (37%), female (36%) or mixed (16%) factors were identified. Based on the AMH level and AFC at day 3 of menstrual cycle, 94 of the 100 patients had a normal ovarian reserve and 6 had low functional ovarian reserve (LFOR). Basal FSH, LH and E2 levels were quantified also at day 3 of the menstrual cycle in each patient (Table 1).

TABLE 1

CfDNA level in follicular fluid pools according to the patients' clinical characteristics.

| Variable | Mean | n (total = 100) | Min-Max | SD | FF cfDNA (ng/μl) Mean ± SD [95% CI] | p-value |
|---|---|---|---|---|---|---|
| Age (years) | 34.3 | — | 23-43 | 4.5 | — | — |
| <37 years | — | 64 | — | — | 1.9 ± 2.7 [0.1-2.5] | 0.19 NS |
| ≥37 years | — | 36 | — | — | 1.5 ± 1.0 [1.1-1.8] | |
| BMI (kg/m$^2$) | 23.3 | — | 17-39 | 4.2 | — | — |
| 18.5 ≤ BMI < 25 | — | 58 | — | — | 1.9 ± 2.6 [1.2-2.6] | ref |
| BMI <18.5 | — | 10 | — | — | 1.2 ± 1.1 [0.4-1.9] | 0.54 NS |
| 25 ≤ BMI < 30 | — | 24 | — | — | 1.7 ± 1.6 [1.0-2.4] | 0.56 NS |
| BMI ≥30 | — | 8 | — | — | 1.6 ± 1.5 [0.3-2.8] | 0.93 NS |
| Infertility length (years)* | 3.5 | — | 1-9 | 1.7 | — | — |
| 1 | — | 8 | — | — | 1.1 ± 1.6 [0-2.4] | ref |
| 2-4 | — | 68 | — | — | 1.4 ± 1.3 [1.1-1.7] | 0.08 NS |
| ≥5 | — | 23 | — | — | 2.9 ± 3.8 [1.3-4.5] | **0.049** |
| Infertility aetiology | | | | | | |
| Male factor | — | 37 | — | — | 1.5 ± 1.1 [1.1-1.9] | ref |
| Female factor | — | 36 | — | — | 1.9 ± 2.1 [1.2-2.6] | 0.72 NS |
| Tubal alterations (%) | — | 9 (25) | — | — | 1.3 ± 1.6 [0.1-2.5] | 0.28 NS |
| Endometriosis (%) | — | 21 (58.3) | — | — | 2.1 ± 2.5 [0.9-3.2] | 0.67 NS |
| Ovulatory dysfunction (%) | — | 1 (2.8) | — | — | — | — |
| Ovarian disorders (%) | — | 4 (11.1) | — | — | 2.3 ± 1.3 [0.1-4.4] | 0.28 NS |
| Uterine factor (%) | — | 1 (2.8) | — | — | — | — |
| Mixed infertility | — | 16 | — | — | 1.7 ± 3.1 [0.1-3.4] | 0.08 NS |
| Unexplained infertility | — | 11 | — | — | 2.0 ± 3.7 [0-4.5] | 0.23 NS |
| Primary infertility | — | 61 | — | — | 2.1 ± 2.7 [1.5-2.8] | 0.08 NS |
| Secondary infertility | — | 39 | — | — | 1.1 ± 0.8 [0.8-1.4] | |
| IVF/ICSI cycle number | 2.1 | — | 1-4 | 1.3 | — | — |
| 1 | — | 39 | — | — | 1.2 ± 0.9 [0.9-1.5] | 0.39 NS |
| >1 | — | 61 | — | — | 2.1 ± 2.7 [1.4-2.8] | |
| Baseline evaluation | | | | | | |
| FSH (IU/l)* | 7.4 | — | 0.1-19 | 2.4 | — | — |
| <10 | — | 87 | — | — | 1.6 ± 2.0 [1.2-2.1] | 0.42 NS |
| ≥10 | — | 12 | — | — | 2.4 ± 3.7 [0-4.7] | |
| LH (IU/l)* | 5.7 | — | 1-11.2 | 1.9 | — | — |
| 3-5 | — | 32 | — | — | 1.4 ± 1.3 [0.9-1.8] | ref |
| <3 | — | 5 | — | — | 2.0 ± 1.0 [0.7-3.3] | 0.1 NS |
| >5 | — | 60 | — | — | 1.8 ± 2.6 [1.1-2.4] | 0.7 NS |
| E2 (pg/ml)* | 40.7 | — | 4-99 | 17.8 | — | — |
| ≤45 | — | 66 | — | — | 1.8 ± 2.5 [1.2-2.5] | 0.56 NS |
| >45 | — | 32 | — | — | 1.5 ± 1.6 [1.0-2.1] | |
| AMH (ng/ml)* | 2.7 | — | 0.2-8.6 | 1.6 | — | — |
| ≤1 | — | 5 | — | — | 4.3 ± 5.0 [0-10.4] | 0.06 NS |
| >1 | — | 90 | — | — | 1.6 ± 2.0 [1.2-2.0] | |
| AFC* | 13.7 | — | 3-25 | 5.7 | — | — |
| <10 | — | 24 | — | — | 2.3 ± 2.6 [1.2-3.4] | **0.04** |
| ≥10 | — | 63 | — | — | 1.5 ± 2.2 [1.0-2.1] | |
| Normal ovarian reserve | — | 94 | — | — | 1.7 ± 2.3 [1.3-2.2] | ref |

TABLE 1-continued

CfDNA level in follicular fluid pools according to the patients' clinical characteristics.

| Variable | Mean | n (total = 100) | Min-Max | SD | FF cfDNA (ng/µl) Mean ± SD [95% CI] | p-value |
|---|---|---|---|---|---|---|
| Ovarian insufficiency | — | 6 | — | — | 2.1 ± 1.4 [0.6-3.6] | 0.29 NS |
| Agonist protocol** | — | 48 | — | — | 1.4 ± 2.0 [0.9-2.0] | 0.09 NS |
| Antagonist protocol | — | 50 | — | — | 1.8 ± 1.8 [1.3-2.3] | |
| Ovarian stimulation treatment | | | | | | |
| Days of stimulation | 10 | — | 7-14 | 1.2 | — | — |
| 7-10 | — | 71 | — | — | 1.5 ± 1.9 [1.0-1.9] | **0.008** |
| >10 | — | 29 | — | — | 2.4 ± 2.8 [1.4-3.5] | |
| Total dose of gonadotropins (IU/l) | 2414.7 | — | 875-4950 | 932.5 | — | — |
| <3000 | — | 66 | — | — | 1.5 ± 2.1 [1.0-2.0] | **0.01** |
| ≥3000 | — | 34 | — | — | 2.2 ± 2.3 [1.4-3.0] | |
| Agonist protocol | | | | | | |
| Days of stimulation | 10 | — | 8-14 | 1.1 | | |
| 8-10 | — | 37 | — | — | 1.1 ± 1.1 [0.7-1.4] | 0.05 NS |
| >10 | — | 11 | — | — | 2.7 ± 3.6 [0.3-5.1] | |
| Total dose of gonadotropins (IU/l) | 2324 | — | 900-4200 | 797.8 | | |
| <3000 | — | 34 | — | — | 1.1 ± 1.1 [0.7-1.5] | **0.049** |
| ≥3000 | — | 14 | — | — | 2.4 ± 3.2 [0.5-4.2] | |
| Antagonist protocol | | | | | | |
| Days of stimulation | 10 | — | 7-13 | 1.2 | | |
| 7-10 | — | 33 | — | — | 1.5 ± 1.6 [1.0-2.1] | 0.11 NS |
| >10 | — | 17 | — | — | 2.2 ± 2.3 [1.0-3.4] | |
| Total dose of gonadotropins (IU/l) | 2475.5 | — | 875-4950 | 982.7 | | |
| <3000 | — | 31 | — | — | 1.6 ± 2.0 [0.9-2.3] | 0.13 NS |
| ≥3000 | — | 19 | — | — | 2.0 ± 1.6 [1.3-2.8] | |
| Hormonal ovarian response at ovulation triggering | | | | | | |
| Peak E2 level (pg/ml) | 1793.2 | — | 341-4768 | 799 | — | — |
| 1000-2000 | — | 56 | — | — | 1.8 ± 2.1 [1.2-2.3] | ref |
| <1000 | — | 12 | — | — | 2.4 ± 3.5 [0.2-4.6] | 0.71 NS |
| >2000 | — | 32 | — | — | 1.4 ± 1.8 [0.8-2.1] | 0.23 NS |
| Progesterone level (ng/ml) | 0.8 | — | 0.1-1.6 | 0.3 | — | — |
| <1 | — | 76 | — | — | 1.7 ± 2.1 [1.2-2.2] | 0.82 NS |
| ≥1 | — | 24 | — | — | 1.8 ± 2.6 [0.7-2.9] | |
| LH level (IU/l) | 2.0 | — | 0.1-6.0 | 1.5 | — | — |
| <2 | — | 38 | — | — | 1.9 ± 2.0 [1.3-2.6] | 0.62 NS |
| ≥2 | — | 24 | — | — | 2.3 ± 3.5 [0.8-3.7] | |
| IVF | — | 31 | — | — | 1.7 ± 2.4 [0.8-2.5] | 0.44 NS |
| ICSI | — | 69 | — | — | 1.8 ± 2.2 [1.3-2.3] | |

SD, standard deviation;
BMI, body mass index;
FSH, follicle-stimulating hormone;
LH, luteinizing hormone;
E2, 17β-estradiol;
AMH, anti-Müllerian hormone;
AFC, antral follicle count.
*Total number of patients <100.
P-values: Mann-Whitney test.

In addition, cfDNA was quantified also in FF pools from 17 women with PCOS who were classified according the Rotterdam criteria (Rotterdam ESHRE/ASRM-Sponsored PCOS consensus workshop group. Revised 2003 consensus on diagnostic criteria and long-term health risks related to polycystic ovary syndrome (PCOS). Hum Reprod 2004; 19: 41-7). The clinical characteristics of PCOS patients are reported separately in S1 Table.

Each patient's written informed consent for FF sample collection/analysis was obtained on oocyte retrieval day. This study was approved by the Ethical Committee of the Institute for Regenerative Medicine and Biotherapy and the methods were carried out in accordance with the approved guidelines.

In Vitro Fertilization Protocol and Follicular Fluid Sample Collection

Forty-eight patients received a daily GnRH agonist protocol (Decapeptyl, IpsenPharma) and the others an antagonist protocol. These two protocols included ovarian stimulation by recombinant FSH (r-FSH) (Puregon, MSD, Courbevoie, France). The ovarian response to stimulation was monitored by quantifying serum E2 level and by ultrasound assessment of follicular and endometrial growth. The ovarian stimulation length was 10±1.2 day and the total gonadotropin dose was 2414.7±932.5 IU/l (mean±SD) (Table 2). Ovulation was triggered by a single injection of 250 µg human chorionic gonadotropin (hCG) (Ovitrelle, Merck Serono, Lyon, France), when at least three follicles reached the diameter of 17 mm or more on ultrasound examination.

TABLE 2

CfDNA level in follicular fluid pools according to COS protocols and ovarian response to stimulation.

| Variable | Mean | n (total = 100) | Min-Max | SD | FF cfDNA (ng/μl) Mean ± SD [95% CI] | p-value |
|---|---|---|---|---|---|---|
| Agonist protocol** | — | 48 | — | — | 1.4 ± 2.0 [0.9-2.0] | 0.09 NS |
| Antagonist protocol | — | 50 | — | — | 1.8 ± 1.8 [1.3-2.3] | |
| Ovarian stimulation treatment | | | | | | |
| Days of stimulation | 10 | — | 7-14 | 1.2 | — | — |
| 7-10 | — | 71 | — | — | 1.5 ± 1.9 [1.0-1.9] | **0.008** |
| >10 | — | 29 | — | — | 2.4 ± 2.8 [1.4-3.5] | |
| Total dose of gonadotropins (IU/l) | 2414.7 | — | 875-4950 | 932.5 | — | — |
| <3000 | — | 66 | — | — | 1.5 ± 2.1 [1.0-2.0] | **0.01** |
| ≥3000 | — | 34 | — | — | 2.2 ± 2.3 [1.4-3.0] | |
| Agonist protocol | | | | | | |
| Days of stimulation | 10 | — | 8-14 | 1.1 | | |
| 8-10 | — | 37 | — | — | 1.1 ± 1.1 [0.7-1.4] | 0.05 NS |
| >10 | — | 11 | — | — | 2.7 ± 3.6 [0.3-5.1] | |
| Total dose of gonadotropins (IU/l) | 2324 | — | 900-4200 | 797.8 | | |
| <3000 | — | 34 | — | — | 1.1 ± 1.1 [0.7-1.5] | **0.049** |
| ≥3000 | — | 14 | — | — | 2.4 ± 3.2 [0.5-4.2] | |
| Antagonist protocol | | | | | | |
| Days of stimulation | 10 | — | 7-13 | 1.2 | | |
| 7-10 | — | 33 | — | — | 1.5 ± 1.6 [1.0-2.1] | 0.11 NS |
| >10 | — | 17 | — | — | 2.2 ± 2.3 [1.0-3.4] | |
| Total dose of gonadotropins (IU/l) | 2475.5 | — | 875-4950 | 982.7 | | |
| <3000 | — | 31 | — | — | 1.6 ± 2.0 [0.9-2.3] | 0.13 NS |
| ≥3000 | — | 19 | — | — | 2.0 ± 1.6 [1.3-2.8] | |
| Hormonal ovarian response at ovulation triggering | | | | | | |
| Peak E2 level (pg/ml) | 1793.2 | — | 341-4768 | 799 | — | — |
| 1000-2000 | — | 56 | — | — | 1.8 ± 2.1 [1.2-2.3] | ref |
| <1000 | — | 12 | — | — | 2.4 ± 3.5 [0.2-4.6] | 0.71 NS |
| >2000 | — | 32 | — | — | 1.4 ± 1.8 [0.8-2.1] | 0.23 NS |
| Progesterone level (ng/ml) | 0.8 | — | 0.1-1.6 | 0.3 | — | — |
| <1 | — | 76 | — | — | 1.7 ± 2.1 [1.2-2.2] | 0.82 NS |
| ≥1 | — | 24 | — | — | 1.8 ± 2.6 [0.7-2.9] | |
| LH level (IU/l) | 2.0 | — | 0.1-6.0 | 1.5 | — | — |
| <2 | — | 38 | — | — | 1.9 ± 2.0 [1.3-2.6] | 0.62 NS |
| ≥2 | — | 24 | — | — | 2.3 ± 3.5 [0.8-3.7] | |

E2, 17β-estradiol;
LH, luteinizing hormone;
IVF, in vitro fertilization;
ICSI, intracytoplasmic sperm injection.
**except two mild ovarian stimulations.
P-values: Mann-Whitney test.

Oocyte retrieval was performed by transvaginal ultrasound-guided aspiration 36 h after hCG administration and all follicles were aspirated without flushing. All FF samples collected from the same patient were pooled and cumulus-oocyte complexes were isolated for conventional IVF or ICSI procedures.

Before ICSI, cumulus and coronal cells were removed to assess oocyte maturity rate. On average, 9.5±4.7 oocytes (mean±SD) (S2 Table) were obtained and individually maintained in 30 μl micro-droplets of culture medium (Vitrolife) under oil, at 37° C., in 5% $O_2$, 6% $CO_2$, 89% $N_2$ and in humid atmosphere. Oocytes were considered as normally fertilized if two pronuclei and two polar bodies were observed 18-20 h after microinjection or insemination. Early cleavage was checked at 25 or 27 h after microinjection or insemination, respectively. On day 2 and 3, embryo morphology was evaluated by microscopic observation of morphological criteria, such as number of blastomeres, blastomere regularity and fragmentation rate. Embryo quality was graded from 1 to 4, as described in S3 Table. A top quality embryo (grade 1 and 2) was defined as an embryo with 4-5 or 6-8 regular blastomeres, at day 2 or 3, respectively, and containing less than 20% fragments. At day 3, top quality embryos were selected for transfer or freezing, whereas the others were cultured up to day 5 and frozen by vitrification (Irvine Scientific recommendation), according to their quality, assessed by Gardner scoring (Gardner D K, Lane M, Stevens J, Schlenker T, Schoolcraft W B. Blastocyst score affects implantation and pregnancy outcome: towards a single blastocyst transfer. Fertil Steril 2000; 73: 1155-8). Four weeks after transfer, clinical pregnancy was confirmed by the presence of at least one gestational sac and the visualization of embryonic heart activity on ultrasound examination.

Follicular Fluid Preparation

All FF samples from the same patient were pooled and a volume of 15 ml was centrifuged at 3000 g for 15 min. Supernatants were filtered with 0.45 μm filters to eliminate cell debris and then stored at −80° C. until cfDNA quantification. A total of 117 FF pools were collected for this study.

Cell-Free DNA Extraction and Quantification by ALU-qPCR

FF pools were prepared for cfDNA quantification as previously reported (Umetani N, Kim J, Hiramatsu S, Reber H A, Hines O J, Bilchik A J, et al. Increased integrity of free circulating DNA in sera of patients with colorectal or periampullary cancer: direct quantitative PCR for ALU repeats. Clin Chem 2006; 52: 1062-9). Specifically, 20 μl of each FF pool was digested with 16 μg proteinase K (PK) (Qiagen) in 20 μl of buffer (25 ml/l Tween 20, 50 mmol/l Tris and 1 mmol/l EDTA) at 50° C. for 20 min, followed by PK heat inactivation and insolubilization at 95° C. for 5 min. After centrifugation at 10 000 g for 5 min, supernatants were removed and stored at −80° C. for cfDNA quantification.

CfDNA was quantified by qPCR, using ALU 115 primers (Umetani et al., 2006). Each ALU-qPCR reaction included 1 μl of PK-digested FF pool and a reaction mixture containing 0.25 μM of forward and reverse ALU 115 primers and 5 μL of 2× LightCycler®480 SYBR Green I master mix (Roche Applied Science, Germany). CfDNA concentration in FF pools was determined using a standard curve obtained by successive dilutions of genomic DNA (Umetani et al., 2006). A negative control (without template) was integrated in each qPCR plate and each FF pool was analysed in quadruplicate.

Statistical Analysis

Univariate analysis was performed for each variable. Continuous parametric data are presented as mean±standard deviation (SD) and categorical variables as numbers and percentages. The Mann-Whitney test and Spearman correlations were used to compare cfDNA levels according to quantitative variables, based on the normality of the distribution assessed using the Shapiro-Wilk test. A multivariate analysis was used to model the clinical pregnancy probability. A logistic regression model was fitted in which all variables associated with a p value lower than 0.20 were included in the univariate analysis. Then, a stepwise procedure allowed obtaining the final multivariate model. The ability of FF cfDNA level to predict the clinical pregnancy outcome was determined by constructing the Receiving Operator Curve (ROC) curve and calculating the area under the curve (AUC) with 95% confidence intervals (CI). The sensitivity and specificity for the optimal cut-off were calculated. Statistical tests were performed using the R (version 2.15.2) software. Results were considered significant when $p \leq 0.05$.

Results

Cell-Free DNA Level in FF Pools in Relation to Ovarian Reserve Status and Infertility Length The cfDNA concentration in FF pools of the 17 patients with polycystic ovary syndrome (PCOS) was significantly higher than in FF pools from patients with normal ovarian reserve (n=94) (2.9±3.1 ng/μl versus 1.7±2.3 ng/μl, p=0.049) (FIG. 8). Overall, cfDNA levels were significantly higher in FF pools from patients with ovarian reserve disorders (including LFOR and PCOS) than in FF pools from women with normal ovarian reserve (2.7±2.7 ng/μl versus 1.7±2.3 ng/μl, p=0.03) (FIG. 5A).

Given the specific PCOS clinical profile, we decided to exclude these 17 patients from the subsequent analysis. Moreover, cfDNA concentrations were significantly higher in FF pools from patients with low AFC (<10) than in samples from women with normal AFC (≥10) (2.3±2.6 ng/μl versus 1.5±2.2 ng/μl, respectively, p=0.04) (FIG. 5B, left panel and Table 1). Likewise, FF cfDNA level tended to be higher in women with very low AMH serum concentration at day 3 of the menstrual cycle (≤1 ng/ml) than in those with AMH>1 ng/ml (4.3±5.0 ng/μl versus 1.6±2.0 ng/μl, respectively, p=0.06) (FIG. 5B, right panel and Table 1).

Finally, FF cfDNA levels progressively increased with the infertility length and were significantly higher in patients who had been trying to conceive for more than five years compared to women who tried only for one year (2.9±3.8 ng/μl versus 1.1±1.6 ng/μl, p=0.049) (FIG. 5C and Table 1).

Cell-Free DNA Concentration in Follicular Fluid Pools According to COS Protocol and Ovarian Response FF cfDNA level did not vary significantly between women who received GnRH agonists and those treated with antagonists (Table 2). On the other hand, it was significantly higher after long ovarian stimulation (>10 days) than after a short treatment (7-10 days) (2.4±2.8 ng/μl versus 1.5±1.9 ng/μl, p=0.008) (FIG. 6A and Table 2). Likewise, Spearman's correlation analysis showed that FF cfDNA level was significantly and positively correlated with the ovarian stimulation length (r=0.2; p=0.04). Moreover, cfDNA level was significantly higher in FF pools from women who received high total dose of gonadotropins (≥3000 IU/l) than in women treated with lower dose (<3000 IU/l) (2.2±2.3 ng/μl versus 1.5±2.1 ng/μl, p=0.01) (FIG. 6B and Table 2). A similar result was obtained when only patients who received an agonist protocol were considered (2.4±3.2 ng/μl versus 1.1±1.1 ng/μl, p=0.049) (Table 2). In addition, FF pools from patients with a low number of retrieved oocytes (≤6) had a significantly higher cfDNA concentration than those from women with higher number of retrieved oocytes (>6) (2.8±3.5 ng/μl versus 1.4±1.5 ng/μl, p=0.045) (FIG. 6C and S2 Table).

Cell-Free DNA Concentration in Follicular Fluid Pools and Embryo Outcomes

At day 2 post-fertilization, oocyte cohorts that gave rise to a small number of embryos (≤2 embryos) were found to be related to FF pools with significantly higher cfDNA level compared to oocyte cohorts from which at least three embryos were obtained (2.5±2.9 ng/μl versus 1.6±2.0 ng/μl, respectively, p=0.03) (FIG. 7A and Table 3). Moreover, 1.8±1.9 and 1.5±1.5 (mean±SD) embryos in each embryo cohort (i.e., embryos obtained for each patient) were considered as top quality (grade 1 and 2) at day 2 and day 3, respectively. At these early cleavage stages, cfDNA concentration was significantly higher in FF pools related to embryo cohorts that included only poor quality embryos (grades 3 and 4), compared to those related to cohorts with at least one top quality embryo (at day 2: 3.0±3.4 ng/μl versus 1.3±1.5 ng/μl, p=0.002; at day 3: 2.5±3.0 ng/μl versus 1.4±1.7 ng/μl, p=0.006, respectively) (FIGS. 7B and 7C, left panels and Table 3). Likewise, Spearman's correlation analysis indicated that there were significant and negative correlations between FF cfDNA concentration and number of top quality embryos (grades 1 and 2) at day 2 and 3 (r=−0.21, p=0.04; r=−0.21; p=0.04, respectively). Moreover, cfDNA level was significantly higher in the FF pools related to embryo cohorts with less than 20% top quality embryos at day 2 and 3 compared to those related to embryo cohorts that included more than 20% top quality embryos (day 2: 2.5±3.1 ng/μl versus 1.3±1.5 ng/μl, p=0.04; day 3: 2.4±3.0 ng/μl versus 1.3±1.4 ng/μl, p=0.02, respectively) (FIGS. 7B and 7C, right panels and Table 3). In addition, the ratio between number of grade 1-2 embryos and the total number of embryos calculated at day 2 and 3 was significantly and negatively correlated with FF cfDNA level (r=−0.27; p=0.01 and r=−0.23; p=0.03, respectively).

Considering each morphological criterion individually at day 3, cfDNA levels tended to be higher in FF pools related to embryos with high fragmentation rate (≥20%) than with low fragmentation rate (<20%) (2.6±3.5 ng/μl versus 1.4±1.3 ng/μl, respectively, p=0.18) (FIG. 7D, left panel and Table 3). Moreover, the ratio between total number of blastomeres and total number of embryos was calculated for each embryo cohort to estimate the global developmental kinetics. At day 3, cfDNA levels were significantly higher in FF pools corresponding to embryo cohorts with a low total blastomere number/total embryo number ratio (<6; delayed development) than in those with normal developmental kinetics (ratio between 6 and 8) (2.8±2.7 ng/μl versus 1.8±2.8 ng/μl, respectively, p=0.02) (FIG. 7D, right panel and Table 3).

TABLE 3

CfDNA levels in follicular fluid pools according to the embryo development outcome at early stages (day 2 and day 3).

| Embryo development outcome | Mean | SD | n | FF cfDNA (ng/μl) Mean ± SD [95% CI] | p-value |
|---|---|---|---|---|---|
| At day 2 | | | | | |
| Total embryo number | 5.3 | 3.7 | — | — | — |
| ≤2 | — | — | 20 | 2.5 ± 2.9 [1.2-3.9] | 0.03 |
| >2 | — | — | 78 | 1.6 ± 2.0 [1.1-2.0] | |
| Grade 1-2 embryos | 1.8 | 1.9 | — | — | — |
| No grade 1-2 | — | — | 26 | 3.0 ± 3.4 [1.7-4.4] | 0.002 |
| ≥1 grade 1-2 | — | — | 65 | 1.3 ± 1.5 [0.9-1.4] | |
| Grade 1-2 embryos/all embryos | 0.3 | 0.28 | — | — | — |
| ratio <0.2 | — | — | 34 | 2.5 ± 3.1 [1.5-3.6] | 0.04 |
| ratio ≥0.2 | — | — | 57 | 1.3 ± 1.5 [0.9-1.7] | |
| At day 3 | | | | | |
| Grade 1-2 embryos | 1.5 | 1.5 | — | — | — |
| No grade 1-2 | — | — | 32 | 2.5 ± 3.0 [1.4-3.6] | 0.006 |
| ≥1 grade 1-2 | — | — | 59 | 1.4 ± 1.7 [1.0-1.8] | |
| Grade 1-2 embryos/all embryos | 0.29 | 0.3 | — | — | — |
| ratio <0.2 | — | — | 39 | 2.4 ± 3.0 [1.4-3.4] | 0.02 |
| ratio ≥0.2 | — | — | 52 | 1.3 ± 1.4 [0.9-1.7] | |
| % fragmentation | 0.19 | 0.11 | — | — | — |
| % fragmentation <20 | — | — | 60 | 1.4 ± 1.3 [1.0-1.7] | 0.18 NS |
| % fragmentation ≥20 | — | — | 31 | 2.6 ± 3.4 [1.3-3.9] | |
| Total blastomere number/total embryo number | | | — | — | — |
| ratio = 6-8 | — | — | 45 | 1.8 ± 2.8 [1.0-2.6] | ref |
| ratio <6 | — | — | 11 | 2.8 ± 2.7 [1.0-4.6] | 0.02 |
| ratio >8 | — | — | 35 | 1.4 ± 1.2 [1.0-1.8] | 0.39 NS |

SD, standard deviation.
P-values: Mann-Whitney test.

Predictive Value of Cell-Free DNA in Follicular Fluid Pools for Clinical Pregnancy Outcome After adjustment for the rank of IVF/ICSI attempts and the number of embryos, FF cfDNA level was significantly and independently associated with the clinical pregnancy outcome [Adjusted Odd Ratio: 0.69 [0.5; 0.96], p=0.03] (Table 4). The area under the ROC curve, which quantifies the clinical pregnancy prediction potential of FF cfDNA concentration, was 0.73 [0.66-0.87] with 88% specificity and 60% sensitivity. On the other hand, the number of top quality embryos (grades 1 and 2) did not predict significantly the clinical pregnancy outcome (p=0.42), suggesting that in our population, the predictive value of FF cfDNA level was higher than the number of top quality embryos.

TABLE 4

Multivariate logistic model showing the prediction of clinical pregnancy according to the cfDNA level in follicular fluid pools.

| Parameters | Crude OR [95% CI] | p-value | Adjusted OR [95% CI]* | p-value |
|---|---|---|---|---|
| | Probability to obtain a clinical pregnancy | | | |
| FF cfDNA (ng/μl) | 0.75 [0.55; 1.03] | 0.08 | 0.69 [0.5; 0.96] | 0.03 |
| IVF/ICSI rank number = 1 vs >1 | 2.5 [1.0; 6.27] | 0.05 | 3.6 [1.3; 9.8] | 0.01 |
| Embryo number | 1.15 [1.0; 1.3] | 0.04 | 1.18 [1.01; 1.37] | 0.03 |

OR, odds ratio;
*Adjusted to the rank of IVF/ICSI attempts and the number of embryos.

Discussion

This study demonstrates that cfDNA content in pooled FF samples from the same patient is significantly related to the woman's ovarian reserve status, suggesting that high FF cfDNA level could reflect a poor follicular micro-environment. It also shows that cfDNA levels were significantly higher in FF pools after a long or strong ovarian stimulation than after a short treatment or stimulation with low doses of gonadotropins. Finally, our data indicate that FF cfDNA could be used to predict the clinical pregnancy outcome. Altogether, our results suggest that FF cfDNA quantification could be considered for improving IVF strategy and outcomes.

CfDNA amount was significantly higher in FF pools from women with long infertility length (more than 5 years). Long infertility length is often associated with increased stress in infertile couples (Chiba H, Mori E, Morioka Y, Kashiwakura M, Nadaoka T, Saito H, et al. Stress of female infertility: relations to length of treatment. Gynecol Obstet Invest 1997; 43: 171-7; Lynch C D, Sundaram R, Maisog J M, Sweeney A M, Buck Louis G M. Preconception stress increases the risk of infertility: results from a couple-based prospective cohort study—the LIFE study. Hum Reprod 2014; 29: 1067-75). Interestingly, a recent study reported that blood cfDNA level was higher in patients undergoing IVF and suffering from stress (Czamanski-Cohen J, Sarid O, Cwikel J, Levitas E, Lunenfeld E, Douvdevani A, et al. Decrease in cell free DNA levels following participation in stress reduction techniques among women undergoing infertility treatment. Arch Womens Ment Health 2014; 17: 251-3). Therefore, a long period of stress, caused by the absence of pregnancy, could lead to an increase of apoptotic events in follicular cells and ultimately to higher FF cfDNA levels. Moreover, it has been shown that relaxation techniques may be beneficial during IVF process, to reduce plasma cfDNA levels and to improve pregnancy outcomes (Czamanski-Cohen et al., 2014).

CfDNA levels were significantly higher in FF pools from women suffering from PCOS or more generally with ovarian reserve disorders (PCOS and LFOR). PCOS is the most common endocrinopathy in reproductive age women. A variety of biochemical abnormalities have been described in this syndrome, such as hyperinsulinaemia, leading to high serum insulin levels, and hyperandrogenism via stimulation of ovarian androgen secretion (Goodarzi M O, Dumesic D A, Chazenbalk G, Azziz R. Polycystic ovary syndrome: etiology, pathogenesis and diagnosis. Nat Rev Endocrinol 2011; 7: 219-31). Recently, it was reported that high insulin concentration promotes apoptosis in primary cultured rat ovarian granulosa cells (Ni X R, Sun Z J, Hu G H, Wang R H. High Concentration of Insulin Promotes Apoptosis of Primary Cultured Rat Ovarian Granulosa Cells Via Its Increase in Extracellular HMGB1. Reprod Sci 2015; 22: 271-7). Therefore, high FF cfDNA content in patients with PCOS could be explained by increased apoptosis in granulosa cells due to hyperinsulinaemia. Moreover, we previously reported that cfDNA levels are significantly higher in small follicles compared to large ones (Scalici E, Traver S, Molinari N, Mullet T, Monforte M, Vintejoux E, et al. Cell-free DNA in human follicular fluid as a biomarker of embryo quality. Hum Reprod 2014; 29: 2661-9). PCOS is associated with follicular maturity abnormalities, such as increased number of small pre-antral follicles (Dewailly D, Andersen C Y, Balen A, Broekmans F, Dilaver N, Fanchin R, et al. The physiology and clinical utility of anti-Mullerian hormone in women. Hum Reprod Update 2014; 20: 370-85; Franks S, Stark J, Hardy K. Follicle dynamics and anovulation in polycystic ovary syndrome. Hum Reprod Update 2008; 14: 367-78). These small follicles could contain high cfDNA levels, thus explaining why cfDNA concentration is high in FF pools from patients with PCOS. We also show that FF cfDNA concentration is high in women with poor ovarian reserve (AFC<10 or AMH≤1 ng/ml) (Jayaprakasan K, Campbell B, Hopkisson J, Johnson I, Raine-Fenning N. A prospective, comparative analysis of anti-Müllerian hormone, inhibin-B, and three-dimensional ultrasound determinants of ovarian reserve in the prediction of poor response to controlled ovarian stimulation. Fertil Steril 2010; 93: 855-64; Ficicioglu C, Cenksoy P O, Yildirim G, Kaspar C. Which cut-off value of serum anti-Müllerian hormone level can predict poor ovarian reserve, poor ovarian response to stimulation and in vitro fertilization success? A prospective data analysis. Gynecol Endocrinol 2014; 30: 372-6). As ovarian reserve decline is caused by accelerated apoptosis in ovary (Spencer S J, Cataldo N A, Jaffe R B. Apoptosis in the human female reproductive tract. Obstet Gynecol Surv 1996; 51: 314-23; Seifer D B, Gardiner A C, Ferreira K A, Peluso J J. Apoptosis as a function of ovarian reserve in women undergoing in vitro fertilization. Fertil Steril 1996; 66: 593-8; Vital Reyes V S, Téllez Velasco S, Hinojosa Cruz J C, Reyes Fuentes A. [Ovarian apoptosis]. Ginecol Obstet Mex 2001; 69: 101-7), this could lead to an important release of DNA fragments within ovarian follicles. Moreover, in order to optimize their ovarian response, women with poor ovarian reserve receive large gonadotropin doses and at oocyte retrieval day, the practitioner would try to aspirate with more assiduity the smaller follicles to increase number of oocytes. Therefore, in this case follicular fluids from smaller follicles would become proportionally more represented in the pool than in normal responders with a synchronized cohort of larger follicles. These observations suggest that cfDNA content in antral follicles could depend on (i) the basal ovarian status (increased cfDNA in the case of ovarian dysfunction) and/or on (ii) the follicular maturity after recruitment by COS protocols.

Indeed, FF cfDNA level was significantly higher after a long COS protocol (>10 days) or after administration of high doses of gonadotropins (≥3000 IU/l). Moreover, the ovarian reserve status strongly influences the ovarian response to COS protocols (Dewailly D, Andersen C Y, Balen A, Broekmans F, Dilaver N, Fanchin R, et al. The physiology and clinical utility of anti-Mullerian hormone in women. Hum Reprod Update 2014; 20: 370-85; Younis J S, Skournik A, Radin O, Haddad S, Bar-Ami S, Ben-Ami M. Poor oocyte retrieval is a manifestation of low ovarian reserve. Fertil Steril 2005; 83: 504-7; La Marca A, Sunkara S K. Individualization of controlled ovarian stimulation in IVF using ovarian reserve markers: from theory to practice. Hum Reprod Update 2014; 20: 124-40). For instance, long or strong ovarian stimulation is currently recommended for women at risk of poor ovarian response (Ficicioglu C, Cenksoy P O, Yildirim G, Kaspar C. Which cut-off value of serum anti-Müllerian hormone level can predict poor ovarian reserve, poor ovarian response to stimulation and in vitro fertilization success? A prospective data analysis. Gynecol Endocrinol 2014; 30: 372-6; Lan V T, Linh N K, Tuong H M, Wong P C, Howles C M. Anti-Müllerian hormone versus antral follicle count for defining the starting dose of FSH. Reprod Biomed Online 2013; 27: 390-9). Accordingly, patients who received long stimulation or high gonadotropin dose partially overlaps with patients with high intra-follicular cfDNA levels related to low ovarian reserve. Moreover, high FF cfDNA level after long or strong stimulation could represent a true effect of COS protocols, with potential harmful consequences on IVF/ICSI outcomes. For instance, strong supra-physiological gonadotropin doses could induce apoptosis of follicular cells (Liu S, Feng H L, Marchesi D, Chen Z J, Hershlag A. Dose-dependent effects of gonadotropin on oocyte developmental competence and apoptosis. Reprod Fertil Dev 2011; 23: 990-6), suggesting the necessity to specifically tailor stimulation treatments to each patient's profile. Conversely, FF cfDNA content did not differ according to the type of COS protocols (agonist versus antagonist). In agreement, similar apoptosis levels were detected in granulosa cells exposed to agonist or antagonist treatments (Lavorato H L, Oliveira J B, Petersen C G, Vagnini L, Mauri A L, Cavagna M, et al. GnRH agonist versus GnRH antagonist in IVF/ICSI cycles with recombinant LH supplementation: DNA fragmentation and apoptosis in granulosa cells. Eur J Obstet Gynecol Reprod Biol 2012; 165: 61-5).

FF cfDNA concentration was also significantly higher in patients from whom few oocytes were retrieved (≤6) (Broekmans F J, Verweij P J, Eijkemans M J, Mannaerts B M, Witjes H. Prognostic models for high and low ovarian responses in controlled ovarian stimulation using a GnRH antagonist protocol. Hum Reprod 2014; 29: 1688-97) or few embryos obtained (≤2). This observation confirms that high FF cfDNA level is significantly associated with poor ovarian response to COS protocols. Moreover, it suggests that FF cfDNA level is related to both retrieved oocyte quantity and quality, two key features for embryo production. Indeed, it is largely recognized that the follicular environment influences strongly the oocyte developmental competence (Mendoza C, Ruiz-Requena E, Ortega E, Cremades N, Martinez F, Bernabeu R, et al. Follicular fluid markers of oocyte developmental potential. Hum Reprod 2002; 17: 1017-22; Baka S, Malamitsi-Puchner A. Novel follicular fluid factors influencing oocyte developmental potential in IVF: a review. Reprod Biomed Online 2006; 12: 500-6; Revelli A, Delle Piane L, Casano S, Molinari E, Massobrio M, Rinaudo P. Follicular fluid content and oocyte quality: from single biochemical markers to metabolomics. Reprod Biol Endocrinol 2009; 7: 40; Carpintero N L, Suarez O A, Mangas C C, Varea C G, Rioja R G. Follicular steroid hormones as markers of oocyte quality and oocyte development potential. J Hum Reprod Sci 2014; 7: 187-93). For this reason, FF cfDNA could represent a new promising biomarker of follicular microenvironment quality. A poor follicular microenvironment, with high cfDNA levels could affect oocyte developmental competence and embryo development, thus leading to IVF failure. As we found that strong or long ovarian stimulation leads to high FF cfDNA level, it could be recommended to adapt the stimulation length and gonadotropin dose to each patient to limit FF cfDNA production. Indeed, the preservation of the follicular microenvironment is primordial to obtain competent oocytes and thus competent embryos.

This study confirms our previous observation (Scalici et al., 2014) that cfDNA levels in FF samples are significantly correlated with embryo quality during early development, when embryos rely on the oocyte maternal reserve (on day 2 and 3). Indeed, cfDNA levels were significantly higher in FF pools related to oocyte cohorts that gave only poor quality embryos, embryos with high fragmentation rate (≥20%) or developmentally delayed embryos (total blastomere number/total embryo number ratio <6). These poor quality embryos came from oocyte cohorts surrounded by FF containing high cfDNA levels, suggesting a negative effect of a cfDNA-rich follicular environment on embryo quality (Scalici et al., 2014). In agreement with these results, high mitochondrial DNA level in embryo culture medium was also significantly associated with high fragmentation rate at early embryo cleavages (Stigliani S, Anserini P, Venturini P L, Scaruffi P. Mitochondrial DNA content in embryo culture medium is significantly associated with human embryo fragmentation. Hum Reprod 2013; 28: 2652-60).

Finally, FF CfDNA level in a multivariate model predicted independently and significantly the clinical pregnancy outcome with high specificity (88%). FF cfDNA level predictive potential was higher than that of the number of top quality embryos (based on morphological criteria). Therefore, this predictive model could be used as a supplemental tool for determining the chance of IVF success. Recently, a significant association between the mitochondrial DNA/genomic DNA ratio in embryo culture medium and implantation outcome was reported (Stigliani S, Persico L, Lagazio C, Anserini P, Venturini P L, Scaruffi P. Mitochondrial DNA in Day 3 embryo culture medium is a novel, non-invasive biomarker of blastocyst potential and implantation outcome. Mol Hum Reprod 2014; 20: 1238-46). Moreover, Czamanski-Cohen et al. found higher cfDNA level in serum samples from patients with low pregnancy rates after IVF, suggesting that circulating DNA fragments from apoptotic maternal cells could have a damaging effect. As there is fluid components' movement between follicles and vasculature (Rodgers R J, Irving-Rodgers H F. Formation of the ovarian follicular antrum and follicular fluid. Biol Reprod 2010; 82: 1021-9), these fragments could come from massive apoptotic events that occur in the ovaries and that contribute to increasing cfDNA level in FF samples.

In addition, cfDNA quantification in FF pools, fast and easy to perform, could provide an overall picture of the follicular micro-environment quality, influencing IVF outcomes. Therefore, this quantification could be associated with the morphology-based method in order to improve embryo selection for replacement or freezing and consequently the chance of IVF success. This biomarker might constitute a supplemental tool for improving female infertility management and developing a personalized care program.

S1 TABLE

Clinical characteristics and ovarian response to stimulation of patients with polycystic ovary syndrome (PCOS) (n = 17).

| Variable | Mean | n (total = 17) | SD |
|---|---|---|---|
| Age (years) | 33.5 | — | 4.2 |
| <37 years | — | 14 | — |
| ≥37 years | — | 3 | — |
| BMI (kg/m$^2$) | 26.7 | — | 5.9 |
| 18.5 ≤ BMI < 25 | — | 6 | — |
| BMI < 18.5 | — | 1 | — |
| 25 ≤ BMI < 30 | — | 5 | — |
| BMI ≥ 30 | — | 5 | — |
| Infertility lenght (years) | 3.8 | — | 1.3 |
| 1 | — | 1 | — |
| 2-4 | — | 12 | — |
| ≥5 | — | 4 | — |
| Primary infertility | — | 6 | — |
| Secondary infertility | — | 11 | — |
| IVF/ICSI cycle number | 1.9 | — | 1.2 |
| 1 | — | 7 | — |
| >1 | — | 10 | — |
| Baseline evaluation | | | |
| FSH (IU/l) | 5.8 | — | 1.8 |
| LH (IU/l) | 6.9 | — | 3.5 |
| E2 (pg/ml) | 36.3 | — | 15.1 |
| AMH (ng/ml) | 7.4 | — | 3.5 |
| AFC | 26 | — | 11.5 |
| Agonist protocol | — | 13 | — |
| Antagonist protocol | — | 4 | — |
| Days of stimulation | 10 | — | 1.7 |
| Total dose of gonadotropins (IU/l) | 1917.2 | | 751.7 |
| Hormonal ovarian response at ovulation triggering | | | |
| Peak E2 level (pg/ml) | 2068.9 | — | 847.2 |
| Progesterone level (ng/ml) | 0.7 | — | 0.4 |
| LH level (IU/l) | 2.4 | — | 1.8 |

SD, standard deviation; BMI, body mass index; FSH, follicle-stimulating hormone; LH, luteinizing hormone; E2, 17β-estradiol; AMH, anti-Müllerian hormone; AFC, antral follicle count; IVF, in vitro fertilization; ICSI, intracytoplasmic sperm injection.

S2 Table: CfDNA level in follicular fluid pools according to oocyte retrieval, fertilization and early cleavage outcomes.

| Oocyte retrieval, fertilization and early cleavage outcomes | Mean | SD | n | FF cfDNA (ng/μl) Mean ± SD [95% CI] | p-value |
|---|---|---|---|---|---|
| Oocytes | 9.5 | 4.7 | — | — | — |
| ≤6 | — | — | 25 | 2.8 ± 3.5 [1.4-4.2] | **0.045** |
| >6 | — | — | 75 | 1.4 ± 1.5 [1.0-1.7] | |
| Empty zona pellucida | 0.4 | 0.8 | — | — | — |
| No Empty zona pellucida | — | — | 87 | 1.5 ± 1.8 [1.1-1.9] | 0.3 NS |
| ≥1 Empty zona pellucida | — | — | 24 | 2.4 ± 3.2 [1.2-3.7] | |
| Mature oocytes (MII) | 7.2 | 4.1 | — | — | — |
| <5 | — | — | 19 | 2.4 ± 3.1 [1.0-3.9] | 0.25 NS |

-continued

S2 Table: CfDNA level in follicular fluid pools according to oocyte retrieval, fertilization and early cleavage outcomes.

| Oocyte retrieval, fertilization and early cleavage outcomes | Mean | SD | n | FF cfDNA (ng/μl) Mean ± SD [95% CI] | p-value |
|---|---|---|---|---|---|
| ≥5 | — | — | 50 | 1.5 ± 1.6 [1.1-2.0] | |
| Mature oocytes/oocytes | 0.76 | 0.21 | — | — | — |
| ratio <0.75 | — | — | 26 | 1.5 ± 1.5 [0.8-2.1] | 0.45 NS |
| ratio ≥0.75 | — | — | 43 | 2.0 ± 2.4 [1.2-2.7] | |
| Immature oocytes (GV, MI) | 1.8 | 1.9 | — | — | — |
| <3 | — | — | 67 | 1.9 ± 2.5 [1.3-2.5] | 0.97 NS |
| ≥3 | — | — | 33 | 1.4 ± 1.4 [1.0-1.9] | |
| Immature oocytes/oocytes | 0.18 | 0.18 | — | — | — |
| ratio <0.25 | — | — | 70 | 1.9 ± 2.5 [1.3-2.5] | 0.26 NS |
| ratio ≥0.25 | — | — | 30 | 1.3 ± 1.5 [0.8-1.9] | |
| Atretic oocytes | 0.3 | 0.8 | — | — | — |
| No atretic oocyte | — | — | 85 | 1.7 ± 2.3 [1.2-2.3] | 0.44 NS |
| ≥1 atretic oocyte | — | — | 15 | 1.7 ± 1.3 [1.0-2.4] | |
| Atretic oocytes/oocytes | 0.02 | 0.07 | — | — | — |
| ratio ≤0.1 | — | — | 88 | 1.7 ± 2.3 [1.2-2.2] | 0.19 NS |
| ratio >0.1 | — | — | 12 | 1.9 ± 1.3 [1.0-2.7] | |
| Fertilization | | | | | |
| % IVF/ICSI fertilization | 0.65 | 0.3 | — | — | — |
| <0.65 | — | — | 20 | 1.9 ± 1.7 [1.2-2.7] | 0.27 NS |
| ≥0.65 | — | — | 79 | 1.7 ± 2.4 [1.2-2.2] | |
| At 25-27 hours after fertilization | | | | | |
| Early cleavage | 1.8 | 2.6 | — | — | — |
| No | — | — | 36 | 1.9 ± 2.7 [1.0-2.9] | 0.72 NS |
| ≥1 | — | — | 55 | 1.7 ± 2.0 [1.1-2.2] | |
| Early cleavage/2PN | 0.41 | 0.88 | — | — | — |
| ratio ≤0.5 | — | — | 68 | 2.0 ± 2.6 [1.4-2.6] | 0.18 NS |
| ratio >0.5 | — | — | 21 | 1.0 ± 0.8 [0.7-1.4] | |
| % fragmentation | 0.07 | 0.09 | — | — | — |
| <10% | — | — | 31 | 1.3 ± 1.3 [0.9-1.8] | 0.25 NS |
| ≥10% | — | — | 24 | 2.1 ± 2.6 [1.0-3.2] | |

SD, standard deviation;
MII, oocyte blocked in meiotic metaphase II;
GV, germinal vesicle;
MI, oocyte blocked in meiotic metaphase I;
IVF, in vitro fertilization;
ICSI, intracytoplasmic sperm injection.
P-values: Mann-Whitney test.

S3 Table: Embryo quality classification at day 2 and day 3 post-fertilization.

| Morphological criteria | grade 1 | 2 | 3 | | 4 |
|---|---|---|---|---|---|
| Number of blastomeres | | | | | |
| Day 2 | 4-5 | 4-5 | 4-5 | <4 or >5 | — |
| Day 3 | 6-8 | 6-8 | 6-8 | <6 or >8 | — |
| Blastomere regularity | Regular | Regular | Regular or irregular | Regular or irregular | Regular or irregular |
| Fragmentation rate (%) | ≤10 | 10-19 | 20-40 | <40 | >40 |

Embryo quality was graded from 1 to 4 (1-2 for top quality embryos; 3-4 for poor quality embryos), based on the following morphological criteria: number of blastomeres, blastomere regularity and fragmentation rate

Example 3

Materials and Methods

Patients

This prospective study included 131 women who underwent conventional IVF (n=32) or ICSI (n=99) at the ART-PGD Department of the University Hospital of Montpellier, France. Their mean age was 34.7±4.5 years (mean±SD; range: 19 to 43 years) and the body mass index (BMI) was 23.4±4.5 kg/m$^2$ (mean±SD; range: 17 and 37.5 kg/m$^2$) (Table 7). The infertility length was 3.6±1.5 years (mean±SD) and infertility was primary in 78 couples and secondary in the other 53. Male, female and mixed factors were detected in 31.3%, 37.4% and 25.2% of cases, respectively, while infertility was unexplained in 6.1% of couples. This was the first IVF or ICSI attempt for 38.9% of them, while 61.1% had already undergone at least one cycle (mean number of cycles±SD: 2.1±1.3). Among the 131 women, 91 had a normal ovarian reserve and 10 had LFOR, based on the serum AMH level and AFC, evaluated at day 3 of the menstrual cycle. The other 30 women had PCOS, according to the Rotterdam criteria (Rotterdam, 2004). Basal follicle-stimulating hormone (FSH), luteinizing hormone (LH) and 17βestradiol (E2) serum levels were also measured in each patient at day 3 of the menstrual cycle. The clinical characteristics of all women and in the three groups (normal ovarian reserve, PCOS and LFOR) are detailed in Table 7.

Patients were informed about FF sample collection/analysis and they gave their written informed consent on oocyte retrieval day. The local Institutional Review Board approved this investigation.

IVF Procedure

A gonadotropin-releasing hormone (GnRH) agonist (Decapeptyl, IpsenPharma) was administered daily to 63 women and an antagonist protocol was used in 64. The remaining four patients received a mild treatment and were thus excluded from the analysis concerning the treatment effect on miRNA expression. These two protocols included COS with two types of gonadotropins: recombinant FSH (r-FSH) (Puregon, MSD, Courbevoie, France or GonalF, Merck Serrono, Lyon, France), or highly purified human menopausal gonadotropin (hMG) (Menopur, Ferring, Gentilly, France). COS duration was 10.5±1.4 days and the total gonadotropin dose was 2501±673 IU/l (mean±SD) (Table 7). The ovarian response to stimulation was monitored by measuring the serum E2 concentration and by ultrasound assessment of follicular and endometrial growth. Ovulation was triggered with an injection of 250 μg human chorionic gonadotropin (hCG) (Ovitrelle, Merck Serono, Lyon, France) when at least three follicles reached the diameter of 17 mm or more on ultrasound examination. At ovulation triggering day, the hormonal ovarian response was also evaluated by quantifying serum E2, LH and progesterone levels (Table 7).

Oocytes were retrieved by transvaginal ultrasound-guided aspiration 36 h after hCG injection. For each patient, all follicles were aspirated without flushing, cumulus-oocyte complexes were isolated for conventional IVF or ICSI and all FF samples were collected.

Before intracytoplasmic sperm microinjection, the oocyte maturity rate (77%) was assessed after denudation. On average, 7.6±4.5 oocytes (mean±SD) and 6±3.7 mature oocytes (MII) (mean±SD) were collected per patient (Table 8). Oocytes were cultured individually in 30 μl microdroplets of culture medium (Vitrolife) under oil at 37° C. in 5% $O_2$, 6% $CO_2$ and 89% $N_2$, in humid atmosphere. The presence of two pronuclei and two polar bodies, 18-20 h after microinjection or insemination confirmed that the cultured oocytes were normally fertilized (overall fertilization rate=64%). For each patient, 4.1±3.3 embryos were obtained from the fertilized oocytes at day 2. Among these embryos, 1.3±1.4 were cleaved early at 25 or 27 h after microinjection or insemination, respectively. On day 3, embryo quality was assessed based on morphological criteria (blastomere number, blastomere regularity and fragmentation rate). On average, 1.2±1.6 embryos/patient (mean±SD) were considered as top quality because they contained 6-8 regular blastomeres and less than 20% fragments. One or two top quality embryos were transferred in utero at day 3, whereas the others were further cultured up to day 5. Blastocysts were classified according to the scoring system developed by Gardner (Gardner et al., 2000). At day 5, only expanded blastocysts (classified as grade 4 or 5) with inner cell mass and trophectoderm scored as A or B were vitrified using a closed system, following the procedure recommended by Irvine Scientific. Four weeks after embryo transfer, clinical pregnancy was confirmed by the observation of at least one gestational sac and of embryonic heart activity on ultrasound examination. The IVF/ICSI outcomes of all women and in the three groups (normal ovarian reserve, PCOS and LFOR) are reported in Table 8.

FF Sample Preparation

At oocyte retrieval day, all FF samples of a patient were collected and pooled (n=131 pools). A volume of 15 ml from each pool was centrifuged at 3000 g for 15 min. Then, supernatants were removed, filtered through 0.45 μm filters to eliminate cell debris and stored at −80° C.

MiRNA Extraction

The QIAamp® Circulating Nucleic Acid kit (ref 55114; Qiagen) was used for isolation and purification of circulating miRNAs from 3 ml of each FF pool according to the manufacturer's protocol. Briefly, 3 ml of FF pool, 400 μl of Qiagen Proteinase K and 4.2 ml of buffer ACL were mixed by pulse vortexing and incubated at 60° C. for 30 min. After incubation, 9 ml of buffer ACB was added to the lysate and mixed by pulse vortexing. The mixture was then transferred in a QIAamp Mini column by vacuum pressure to adsorb the miRNAs onto a small silica membrane. Next, each membrane was washed in three steps to remove residual contaminants. Highly pure circulating microRNAs were eluted within 40 μl of buffer AVE.

FF miRNA Expression Analysis by RT-qPCR

Complementary DNA (cDNA) was generated using the TaqMan MicroRNA reverse transcription kit and miRNA-specific stem-loop primers for let-7b, miR-29a, miR-30a, miR-140, miR-191 and miR-320a (ref 4427975, Life Technologies). The 15 μl reaction mix contained 5 μl of FF pool, 0.15 μl of 100 mM dNTP, 1.5 μl of 10×RT Buffer, 1 μl of MultiScribe RT enzyme (50 U/μl), 0.19 μl of RNase inhibitor (20 U/μl), 4.16 μl of nuclease-free water and 3 μl of Taqman RT primer. Reverse transcription was carried out at 16° C. for 30 min and then at 42° C. for 30 min, followed by an inactivated step at 85° C. for 5 min and an hold step at 4° C. Quantitative PCR was performed in duplicate for each sample using LightCycler 480® (Roche Applied Science, Germany); a negative control (water) was added for each FF pool. PCR reactions were carried out in a total volume of 10 μl, consisting of 3 μl of cDNA, 5 μl of Taqman Universal PCR MasterMix (Applied Biosystems) and 2 μl of primer (Life Technologies). The mixture was incubated in a 384-well plate, at 95° C. for 10 min, followed by 50 cycles at 95° C. for 15 s and 60° C. for 1 min. Moreover, miR-16 was used as an internal control, due to its stability in body fluids (Kroh et al., 2010; Song et al., 2012), to normalize the miRNA expression levels. The relative expression of the six miRNAs (let-7b, miR-29a, miR-30a, miR-140, miR-191 and miR-320a) in each FF pool was calculated relative to that of miR-16 by using the equation $2^{-\Delta Ct}$, in which ΔCt was determined by the formula: Ct target miRNA−Ct miR-16.

These six miRNAs were chosen because previous studies reported that they are expressed in FF (Sang et al., 2013; Feng et al., 2015).

Pathway Analysis

Pathway Studio® (Elsevier) was used to identify the biological processes in which the miRNAs detected in FF pools are involved in the reproductive system. Key pathways included follicular development, cell proliferation, apoptosis, steroidogenesis, meiosis and embryo implantation. The interactions between some miRNAs and steroid hormones were also integrated in this pathway analysis.

Statistical Analysis

Univariate analysis was performed for each variable. Continuous parametric data are presented as the mean±standard deviation (SD) and categorical variables with numbers and percentages. The Mann-Whitney test, Student's t test, Anova or Kruskal Wallis test were used for quantitative variables, based on the normality of the distribution, assessed using the Shapiro-Wilk test. Multivariate analysis was used to investigate differential miRNA expression related to ovarian reserve disorders (PCOS and LFOR). A logistic regression model was fitted in which all variables associated with a p value lower than 0.20 were included in the univariate analysis. Then, a stepwise procedure allowed obtaining the final multivariate model. The ability of FF miRNA levels to predict ovarian reserve disorders (PCOS and LFOR), blastocyst and clinical pregnancy outcomes was assessed by constructing the Receiver Operating Characteristic (ROC) curves and calculating the area under the ROC curve (AUC) with 95% confidence interval (CI). The sensitivity and specificity of the optimal cut-off were calculated. Statistical tests were performed using the R software (version 2.15.2). Results were considered significant when $p \leq 0.05$.

Results

MiRNA Differential Expression in FF Samples from Women with PCOS Compared to Women with Normal Ovarian Reserve Comparison of the expression profiles showed that miR-30a was significantly up-regulated (p=0.006), while miR-140 and let-7b were significantly down-regulated (p=0.01 for both) in FF pools from patients with PCOS compared to women with normal ovarian reserve (FIG. 9). Moreover, these three miRNAs were significantly and independently associated with PCOS in multivariate analysis (adjusted odds ratio, AOR: 5.0 [1.86; 13.68], p=0.001; 0.52 [0.29; 0.94], p=0.03; 1.0 [0.99; 1.0], p=0.02, respectively) (Table 5). Then, the sensitivity and specificity of the relationship between FF miR-30a, miR-140 and let-7b differential expression and PCOS were determined using the ROC curve analysis and by calculating the AUC. The AUC values for the individual performance of FF miR-30a, FF miR-140 and FF let-7b expression profiles in PCOS discrimination were 0.67 (0.57-0.76), 0.67 (0.57-0.76) and 0.67 (0.57-0.76) (p=0.02, p=0.007, p=0.003), respectively (Table 6). By combining the three miRNAs in multivariate analysis, the AUC value increased to 0.83 (0.73-0.92) (p<0.0001) (Table 6). Moreover, the sensitivity and the specificity of FF miR-30a, FF miR-140 and FF let-7b were 57.7%, 57.7% and 53.9% and 85.1%, 81.1% and 75.7%, respectively (Table 6). The combination of these three miRNAs increased the sensitivity of the prediction to 70% with a specificity of 83.8%. These results indicate that the combination of miR-30a, miR-140 and let-7b, which are differentially expressed in FF samples from patients with PCOS compared to women with normal ovarian reserve, gives the largest AUC value with high sensitivity and specificity, and suggest that these three miRNAs represent new potential PCOS biomarkers.

MiRNA Differential Expression in FF Samples from Women with LFOR Compared to Women with Normal Ovarian Reserve Comparison of mRNA expression in FF pools from women with LFOR and with normal ovarian reserve showed that miR30a and miR-191 were up-regulated (p=0.01 for both) in the LFOR group compared to patients with normal ovarian reserve (FIGS. 9A and 9D). However, a significant and positive association was found only between FF miR-191 expression and LFOR, using a logistic regression model [Crude odds ratio, COR: 1.4 [1.03; 1.93], p=0.03] (Table 5). The AUC values of the individual discrimination power of FF miR-30a and miR-191 for LFOR prediction were 0.79 (0.68-0.87) and 0.77 (0.67-0.86) (p<0.0001, p=0.002) (Table 6). The combination of these two miRNAs improved LFOR detection and the corresponding AUC reached 0.84 (0.67-0.86) with a p-value <0.0001 (Table 6). In addition, this combination was very sensitive (85.9%) and specific (71.4%) (Table 6), suggesting that, together, miR-30a and miR-191 are new promising biomarkers for the identification of women with LFOR.

Differential Expression of FF miRNAs According to the Gonadotropin Treatment and Ovarian Response.

The expression of the six miRNAs was comparable in FF pools from women who received agonist or antagonist protocols. Conversely, FF expression of miR-29a and miR-140 varied significantly according to the gonadotropin treatment. Specifically, miR-29a expression was significantly decreased and miR-140 expression significantly increased in FF pools from women treated with hMG compared with patients who were stimulated with r-FSH (p=0.03; p=0.02, respectively) (FIG. 10A). Moreover, whatever the type of gonadotropin, miR-140 was significantly up-regulated in FF pools from women who received higher total doses of gonadotropins (≥3000 IU/l) compared to those treated with lower doses (<3000 IU/l) (p=0.03) (FIG. 10B). Likewise, Spearman's correlation analysis showed that FF miR-140 level was significantly and positively associated with the total dose of gonadotropins (r=0.21; p=0.02).

At oocyte retrieval day, miR-320a level in FF pools was significantly and positively correlated with the number of mature oocytes (MII) (r=0.24; p=0.02). FF pools from women with a low number of mature oocytes (≤2) contained significant lower FF miR-320 levels than those related to a number of mature oocytes higher than 2 (p=0.04) (FIG. 10C).

FF let-7b Expression and Blastocyst Development

By considering only the group of women with normal ovarian reserve (n=91), we found a significant and negative correlation between FF let-7b expression level and blastulation rate (r=−0.33, p=0.003) Indeed, low FF let-7b expression was significantly associated with the probability to obtain a blastocyst [COR=1.0 [0.99; 1.0], p=0.04]. The AUC value of FF let-7b potential to predict blastocyst development, was 0.66 (0.55-0.76) with 77.2% sensitivity and 59.1% specificity (p=0.02; at cut-off value ≤273.2). Likewise, FF let-7b levels were also correlated significantly and negatively with the expanded blastocyst rate in women with normal ovarian reserve (r=−0.28, p=009). The probability to obtain an expanded blastocyst was significantly associated with intra-follicular expression of let-7b [COR=1.0 [0.99; 1.0], p=0.02]. In addition, the AUC value that defined the performance of FF let-7b in predicting the formation of expanded blastocysts was 0.67 (0.54-0.79), with 70% sensitivity and 64.3% specificity (p=0.02; at cut-off value ≤247.9).

FF miR-29a Predictive Value for Clinical Pregnancy Outcome

In the group with normal ovarian reserve (n=91), FF miR-29a expression predicted significantly the clinical pregnancy outcome [COR=2.08 [1.0; 4.3], p=0.049]. Moreover, the ROC curve analysis indicated that the performance of FF miR-29a for clinical pregnancy prediction reached 0.68 (0.55-0.79) with a sensitivity of 83.3%, but a low specificity (53.5%) (p=0.01; cut-off value >0.32). In addition, comparison of the discrimination power of FF miR-29a expression and of the top quality embryo percentage for clinical pregnancy prediction showed that the AUC value related to FF miR-29a expression was higher than that for the top quality embryo percentage (AUC=0.59 [0.46-0.72]; p=0.27).

Biological Functions of the Candidate miRNAs in the Reproductive System

MiR-29a, miR-320a, let-7b and miR-30a, identified as differentially expressed in FF pools, are involved in several pathways of the reproductive system. Pathway Studio® was used to generate a schematic view of the different regulatory roles of these miRNAs in reproductive processes, such as follicular growth, apoptosis, steroidogenesis, meiosis and embryo implantation (FIG. 11). The schematic also integrated the interactions with steroid hormones (estrogen and progesterone). The potential functions of these miRNAs, their localization in the ovarian follicle and their primary targets are summarized in Table 9.

Discussion

This study investigated the expression profiles of six circulating miRNAs (let-7b, miR-29a, miR-30a, miR-140, miR-191 and miR-320a) in FF pools from patients undergoing IVF/ICSI procedures and found that they are differentially expressed according to the women's ovarian reserve status, gonadotropin treatments and/or IVF outcomes (FIG. 12). Our data suggest that these circulating miRNAs might represent new powerful tools to monitor IVF, by identifying efficiently women with ovarian reserve disorders (PCOS or LFOR) and by predicting IVF outcomes, such as blastocyst development or clinical pregnancy outcomes.

We demonstrate, for the first time, that the expression of let-7b and miR-140 is significantly decreased whereas miR-30a is up-regulated in FF samples from patients with PCOS. Moreover, the combination of these three miRNAs is significantly associated with PCOS, with high specificity and sensitivity. Therefore, they could constitute new specific biomarkers to easily and efficiently identify women with PCOS. Previous studies reported that let-7b is expressed in granulosa and cumulus cells in mammalian and also human ovaries (Yao et al., 2009; Miles et al., 2012; Zhang et al., 2013; Kim et al., 2013; Assou et al., 2013; Cao et al., 2015). PCOS is characterized by follicular development abnormalities, suggesting that the normal "dialogue" between oocyte and granulosa cells in early growing follicles might be altered (Franks et al., 2008). Accordingly, the significant decrease of FF let-7b expression observed in patients with PCOS might reflect this abnormal folliculogenesis. Indeed, it has been reported that let-7b could play a specific role in ovarian follicular development (Yao et al., 2009; Zhang et al., 2013; Cao et al., 2015). Specifically, let-7b regulates the TGF-β signaling pathway in goat ovary by targeting the activin receptor I and Smad2/3 genes (Zhang et al., 2013). TGF-β dysregulation contributes to reproductive abnormalities in PCOS, such as follicle development perturbation (Raja-Khan et al., 2014). Consequently, let-7b down-regulation in ovarian follicles could lead to TGF-β signaling pathway deregulation and ultimately contribute to PCOS development. Abnormal estrogen receptor (ER) expression could also contribute to poor follicular development and ovulatory failure in PCOS (Jakimiuk et al., 2002). MiR-140 plays a role as tumor suppressor and is down-regulated in breast cancer via ERα signaling (Zhang et al., 2012). These findings suggest that the modifications of ERα expression observed in PCOS might influence negatively miR-140 expression in ovarian follicles. Finally, it has been demonstrated that miR-30a overexpression in cultured human granulosa cells promotes BCL2A1, IER3 and cyclin D2 expression by repressing FOXL-2 (Wang et al., 2015). FOXL-2 encodes a forkhead transcription factor that is essential for ovarian development (Crisponi et al., 2001). FOXL-2 conditional knockout in mouse results in sex-reversed follicles with characteristics of cystic follicles, including elevated androgen production by theca cells and morphological transformation of granulosa cells, like in PCOS (Uhlenhaut et al., 2009; Murphy, 2010). Moreover, androgen-induced hirsutism, described in patients with PCOS, is also observed in women carrying FOXL-2 mutations (Meduri et al., 2010). Based on these observations, we hypothesize that miR-30 overexpression in FF pools from women with PCOS might lead to FOXL-2 inhibition/down-regulation in ovarian follicles, thus promoting PCOS symptom development. Differently from two previous study (Sang et al., 2013; Yin et al., 2014), FF miR-320a expression was not affected in our group of women with PCOS. However, miR-320a expression level was significantly lower in FF pools from women with less than two mature oocytes (≤2) compared with women with more than two mature oocytes. In the mouse, miR-320a knockdown in oocytes decreased significantly the proportion of mature oocytes that developed into embryos (Feng et al., 2015). Taken together, these data suggest that miR-320a is indicative of mature oocyte quantity and quality and that its intra-follicular expression could be modulated by the ovarian response quality of patients undergoing IVF.

We then found that the expression of miR-30a and miR-191 is significantly higher in FF pools from women with LFOR compared to women with normal reserve status. Moreover, the combination of these two circulating miRNAs discriminated significantly women with LFOR, with high sensitivity and specificity. Therefore, they could represent new specific biomarkers for the identification of women with LFOR. We already discussed the link between miR-30a overexpression and FOXL-2 down-regulation in granulosa cells (Wang et al., 2015). Moreover, FOXL-2 expression reduction/ablation or FOXL-2 mutations affect significantly follicle development (Murphy, 2010). Indeed, in mice, FOXL-2 disruption causes ovarian failure by blocking follicle development (Uda et al., 2004). Likewise, FOXL-2 mutations result in POF and infertility in women by depletion of the follicle reserve, which could be due to disruption of the follicle assembly or to elevated recruitment of primordial follicles (Murphy, 2010). Therefore, we hypothesize that miR-30 over-expression in ovarian follicles may cause FOXL-2 gene repression in follicular cells and consequently lead to decreased ovarian reserve. Moreover, miR-191 is an ER target in breast cancer (Nagpal et al., 2013) and a recent study reported that some miRNAs related to breast cancer risk are also associated with ovarian insufficiency risk (Rah et al., 2015).

The FF expression of some miRNAs was also modulated by the gonadotropin treatment. MiR-29a was significantly down-regulated and miR-140 overexpressed in FF pools from women who were stimulated with hMG compared with those treated with r-FSH. This is in agreement with a previous study showing that miR-29a is significantly down-regulated by FSH treatment in cultured rat granulosa cells, thus influencing progesterone production (Yao et al., 2010). Our data suggest that gonadotropin treatments could affect intra-follicular miRNA expression and ultimately IVF efficacy. We also found that total high dose of gonadotropins was associated with miR-140 up-regulation. This probably reflects a potential dose-effect relationship of gonadotropins on FF miR-140 expression profile. Further studies are required to investigate the biological mechanisms involved in gonadotropin effect on the intra-follicular expression of these miRNAs.

The importance of miRNAs in early embryo development has been demonstrated in many mammalian species (Suh and Blelloch, 2011). Although Feng et al., did not observe significant differential expression of let-7b in FF samples according to embryo quality (Feng et al., 2015), we found that FF let-7b level was significantly related to the embryo developmental potential. Indeed, let-7b levels in FF predicted significantly blastocyst formation and expansion in women with normal ovarian reserve. It was previously shown that let-7 can regulate developmental timing in *Caenorhabditis elegans* (Reinhart et al., 2000). However, let-7b role in blastocyst formation remains unclear. FF let-7b might represent a new predictive biomarker of blastocyst development that could be useful to define the best strategy of embryo culture during IVF.

In addition, FF miR-29a levels predicted significantly the clinical pregnancy outcome with higher sensitivity (83.3%) compared to the top quality embryos proportion in our cohort. MiR-29a is highly expressed in rat uterus during embryo implantation and its expression is regulated by blastocyst activation and uterine decidualization (Xia et al., 2014). Interestingly, miR-29a expression might influence pregnancy outcome by acting both on the follicular and endometrial side, supporting the hypothesis that favorable follicular and endometrial environments are necessary for conception.

In conclusion, our study shows that, during IVF, miRNA expression profiling in human FF samples provide biomarkers to efficiently and easily identify ovarian reserve disorders and to predict blastocyst development and clinical pregnancy outcomes. These new potential biomarkers could be used in the daily practice to improve personalized IVF strategies and to identify new therapeutic targets in female infertility management.

TABLE 5

Multivariate logistic model showing the association of specific FF mRNAs with polycystic ovary syndrome (PCOS) and low function ovarian reserve (LFOR).

| FF microRNAs | Univariate analysis: Cudde OR [95% CI] | Univariate analysis: p-value | Multivariate analysis: Adjusted OR [95% CI] | Multivariate analysis: p-value |
|---|---|---|---|---|
| Relative FF microRNAs expression related to PCOS | | | | |
| FF miR-30a | 4.5 [1.94; 10.57] | p < 0.001 | 5.0 [1.86; 13.68] | 0.001 |
| FF miR-140 | 0.6 [0.37; 0.96] | 0.03 | 0.52 [0.29; 0.94] | 0.03 |
| FF let-7b | 1.0 [0.99; 1.0] | 0.01 | 1.0 [0.99; 1.0] | 0.02 |
| Relative FF microRNAs expression related to LFOR | | | | |
| FF miR-30a | 4.0 [0.87; 18.23] | 0.07 | 2.8 [0.56; 13.92] | 0.21 |
| FF miR-191 | 1.4 [1.03; 1.93] | 0.03 | 1.4 [0.98; 1.87] | 0.07 |

OR, Odds ratio, FF, follicular fluid.

TABLE 6

Power of discrimination of FF miRNA expressions for PCOS and LFOR identification. MiRNAs were analyzed individually and in combination.

| | Prediction for PCOS | | | | Prediction for LFOR | | |
|---|---|---|---|---|---|---|---|
| ROC analysis | FF miR-30a | FF miR-140 | FF let-7b | Combination of FF miR-30a, miR-140 and let-7b | FF miR-30a | FF miR-191 | Combination of FF miR-30a and miR-191 |
| AuROC (95% CI) | 0.67 (0.57-0.76) | 0.67 (0.57-0.76) | 0.67 (0.57-0.76) | 0.83 (0.73-0.92) | 0.79 (0.68-0.87) | 0.77 (0.67-0.86) | 0.84 (0.67-0.86) |
| p-value | **0.02** | **0.007** | **0.003** | **<0.0001** | **<0.0001** | **0.002** | **<0.0001** |
| Sensitivity (%) | 57.7 | 57.7 | 53.9 | 70.0 | 100 | 57.1 | 85.9 |
| Specificity (%) | 85.1 | 81.1 | 75.7 | 83.8 | 53.9 | 92.3 | 71.4 |
| Positive predictive value (%) | 57.7 | 51.7 | 41.9 | 60 | 16.3 | 40 | 31.3 |
| Negative predictive value (%) | 85.1 | 84.5 | 81.2 | 88.6 | 100 | 96 | 97.1 |
| Cut-off value | >0.49 | ≤0.92 | ≤93.95 | — | >0.14 | >2.98 | — |

TABLE 7

Clinical characteristics of all patients (n = 131) and of each groups: women with normal ovarian reserve (n = 91), with polycystic ovary syndrome (PCOS) (n = 30), or low function ovarian reserve (LFOR) (n = 10). SD, standard deviation; BMI, body mass index; FSH, follicle-stimulating hormone; LH, luteinizing hormone; E2, 17β-estradiol; AMH, anti-Mullerian hormone; AFC, antral follicle count; r-FSH, recombinant follicle-stimulating hormone; HP-hMG, highly purified human menopausal gonadotropin *Except four women who received mild stimulation.

| | Total (n = 131) | | Normal ovarian reserve (n = 91) | | PCOS (n = 30) | | LFOR (n = 10) | |
|---|---|---|---|---|---|---|---|---|
| Variable | Mean ± SD | n (%) | Mean ± SD | n (%) | Mean ± SD | n (%) | Mean ± SD | n (%) |
| Age (years) | 34.7 ± 4.5 | — | 34.3 ± 5.1 | — | 33.1 ± 3.8 | — | 36.8 ± 4.6 | — |
| BMI (kg/m$^2$) | 23.4 ± 4.5 | — | 22.8 ± 3.7 | — | 25.4 ± 5.3 | — | 22.1 ± 4.6 | — |
| 18.5 ≤ BMI < 25 | — | 83 (63.4) | — | 66 (72.5) | — | 11 (36.7) | — | 7 (70.0) |
| BMI <18.5 | — | 9 (6.9) | — | 4 (4.4) | — | 3 (10.0) | — | 1 (10.0) |
| 25 ≤ BMI < 30 | — | 29 (22.1) | — | 17 (18.7) | — | 11 (36.7) | — | 1 (10.0) |
| BMI ≥30 | — | 10 (7.6) | — | 4 (4.4) | — | 5 (16.6) | — | 1 (10.0) |
| Infertility lenght (years) | 3.6 ± 1.5 | — | 3.3 ± 1.6 | — | 3.9 ± 1.6 | — | 3.8 ± 1.4 | — |
| Infertility aetiology | | | | | | | | |
| Male factor | — | 41 (31.3) | — | 37 (40.6) | — | 2 (6.6) | — | 2 (20.0) |
| Female factor | — | 49 (37.4) | — | 38 (41.8) | — | 8 (26.7) | — | 5 (50.0) |
| Mixed infertility | — | 33 (25.2) | — | 8 (8.8) | — | 20 (66.7) | — | 3 (30.0) |
| Unexplained infertility | — | 8 (6.1) | — | 8 (8.8) | — | 0 (0) | — | 0 (0) |
| Primary infertility | — | 78 (59.5) | — | 57 (62.6) | — | 14 (46.7) | — | 7 (70.0) |
| Secondary infertility | — | 53 (40.5) | — | 34 (37.4) | — | 16 (53.3) | — | 3 (30.0) |
| IVF/ICSI cycle number | 2.1 ± 1.3 | — | 2.2 ± 1.3 | — | 1.9 ± 1.1 | — | 2.2 ± 1.4 | — |
| 1 | — | 51 (38.9) | — | 34 (37.4) | — | 12 (40.0) | — | 5 (50.0) |
| >1 | — | 80 (61.1) | — | 56 (42.7) | — | 18 (60.0) | — | 5 (50.0) |
| Baseline evaluation | | | | | | | | |
| FSH (IU/l) | 8.3 ± 1.8 | — | 7.2 ± 2.3 | — | 6.1 ± 1.7 | — | 11.6 ± 3.1 | — |
| LH (IU/l) | 7.1 ± 3.7 | — | 5.6 ± 2.1 | — | 8.2 ± 4.5 | — | 7.4 ± 4.5 | — |
| E2 (pg/ml) | 47.7 ± 35.2 | — | 45.9 ± 39.2 | — | 41.9 ± 15.4 | — | 55.3 ± 20.9 | — |
| AMH (ng/ml) | 4.1 ± 2.4 | — | 3.1 ± 1.7 | — | 8.0 ± 5.1 | — | 1.1 ± 0.5 | — |
| AFC | 16 ± 6 | — | 16 ± 6 | — | 27 ± 11 | — | 6 ± 2 | — |
| Agonist protocol* | — | 63 (48.1) | — | 39 (42.9) | — | 19 (63.3) | — | 5 (50.0) |
| Antagonist protocol | — | 64 (48.9) | — | 48 (52.7) | — | 11 (36.7) | — | 5 (50.0) |
| Days of stimulation | 10.5 ± 1.4 | — | 10 ± 1.3 | — | 10.4 ± 1.7 | — | 11.1 ± 1.3 | — |
| Total dose of gonadotropins (IU/l) | 2501 ± 673 | — | 2321.7 ± 912.5 | — | 1851.4 ± 706.3 | — | 3330 ± 400.1 | — |
| r-FSH | — | 73 (55.8) | — | 45 (49.4) | — | 24 (80.0) | — | 4 (40.0) |
| HP-hMG | — | 54 (41.2) | — | 42 (46.2) | — | 6 (20.0) | — | 6 (60.0) |
| Hormonal ovarian response at ovulation triggering | | | | | | | | |
| Peak E2 level (pg/ml) | 1552 ± 668.2 | — | 1764.5 ± 728.3 | — | 1656.9 ± 737.6 | — | 1234.7 ± 538.7 | — |
| Progesterone level (ng/ml) | 0.8 ± 0.4 | — | 0.9 ± 0.4 | — | 0.8 ± 0.4 | — | 0.7 ± 0.4 | — |
| LH level (IU/l) | 2.1 ± 1.7 | — | 2.0 ± 1.4 | — | 2.4 ± 2.1 | — | 2.0 ± 1.6 | — |
| FIV | — | 32 (24.4) | — | 23 (25.3) | — | 5 (16.7) | — | 4 (40.0) |
| ICSI | — | 99 (75.6) | — | 68 (74.7) | — | 25 (83.3) | — | 6 (60.0) |

TABLE 8

IVF outcomes of all patients (n = 131) and of each groups: women with normal ovarian reserve (n = 91), with PCOS (n = 30), or LFOR (n = 10). SD, standard deviation; MII, oocyte blocked in meiotic metaphase II.

| | Total (n = 31) | | | Normal ovarian reserve (n = 91) | | | PCOS (n = 30) | | | LFOR (n = 10) | | |
|---|---|---|---|---|---|---|---|---|---|---|---|---|
| IVF outcomes | Mean | SD | n | Mean | SD | n | Mean | SD | n | Mean | SD | n |
| Retrieved oocytes | 7.6 | 4.5 | — | 9.0 | 4.2 | — | 9.1 | 4.8 | — | 4.7 | 4.5 | — |
| Mature oocytes (MII) | 6.0 | 3.7 | — | 7.8 | 4.1 | — | 6.4 | 3.6 | — | 3.7 | 3.4 | — |
| ≤2 | — | — | 14 | — | — | 9 | — | — | 1 | — | — | 4 |
| >2 | — | — | 85 | — | — | 59 | — | — | 24 | — | — | 2 |
| Maturity rate (%) | 77 | — | — | 81 | — | — | 71 | — | — | 80 | — | — |
| IVF/ICSI fertilization rate (%) | 64 | — | — | 67 | — | — | 60 | — | — | 65 | — | — |
| At 25-27 hours after fertilization | | | | | | | | | | | | |
| Early cleavage | 1.3 | 1.4 | — | 2.2 | 2.1 | — | 1.2 | 1.6 | — | 0.5 | 0.5 | — |

TABLE 8-continued

IVF outcomes of all patients (n = 131) and of each groups: women with normal ovarian reserve (n = 91), with PCOS (n = 30), or LFOR (n = 10). SD, standard deviation; MII, oocyte blocked in meiotic metaphase II.

| | Total (n = 31) | | | Normal ovarian reserve (n = 91) | | | PCOS (n = 30) | | | LFOR (n = 10) | | |
|---|---|---|---|---|---|---|---|---|---|---|---|---|
| IVF outcomes | Mean | SD | n | Mean | SD | n | Mean | SD | n | Mean | SD | n |
| At Day 2 | | | | | | | | | | | | |
| Embryo | 4.1 | 3.3 | — | 4.8 | 3.7 | — | 4.6 | 3.3 | — | 2.8 | 3.0 | — |
| At Day 3 | | | | | | | | | | | | |
| Top quality embryo | 1.2 | 1.6 | — | 1.6 | 1.8 | — | 1.2 | 1.7 | — | 0.8 | 1.3 | — |
| Total fragmentation rate (%) | 15 | — | — | 14 | — | — | 17 | — | — | 15 | — | — |
| At Day 5 | | | | | | | | | | | | |
| Blastulation rate (Blastocyst/prolonged culture embryos) (%) | 31 | — | — | 46 | — | — | 38 | — | — | 8 | — | — |
| Expanded blastocyst rate (Expanded blastocyst/blastocysts) (%) | 45 | — | — | 52 | — | — | 38 | — | — | — | — | — |
| Clinical pregancy rate per transfer (%) | 27 | — | — | 38 | — | — | 29 | — | — | 14 | — | — |
| Singleton pregnancy | — | — | 31 | — | — | 22 | — | — | 9 | — | — | 1 |
| Multiple pregnancy | — | — | 2 | — | — | 1 | — | — | 1 | — | — | 0 |

TABLE 9

Circulating miRNAs expressed in the cumulus-oocyte complex (COC), granulosa cells (GC), cumulus cells (CC) and in follicular fluid (FF): their functions and primary targets in ovarian follicles.

| miRNAs | Expression | Species | Regulation | Target genes | Functions | References |
|---|---|---|---|---|---|---|
| let 7b | CC | Human | — | — | Regulation of COC | Assou et al. (2013) |
| | GC | Porcine | — | — | Ovary follicle atresia | Cao et al. (2015) |
| | GC | Mouse | — | — | Follicular development | Yao et al. (2009) |
| | Ovary | Goat | — | Activin receptor I, Smad 2/3 | Follicular development | Zhang et al. (2013) |
| | COC | Bovine | — | — | Oogenesis | Miles et al. (2012) |
| miR-29a | CC | Human | — | DNMT 3A/3B | Meiosis resumption | Santonocito et al. (2014) |
| | GC (culture) | Rat | Regulation by FSH | COL4AI and BMF | Progesterone production | Yao et al. (2010) |
| miR-30a | GC COV43 (culture) | Human | — | FOXL2, BCL2A1, IER3 and cyclin D2 | Cell proliferation | Wang et al. (2015) |
| miR-320a | FF | Human | — | — | Embryo quality | Feng et al. (2015) |
| | FF | Human | — | — | PCOS | Sang et al. (2013) |
| | GC | Mouse | Regulation by FSH and by miR-383 | E2F1 and SF-1 | Cell proliferation, oestrogen secretion | Yin et al. (2014) |
| | Oocytes/ embryos | Mouse | — | Wnt signaling pathway genes | Oocyte quality/Embryo developement | Feng et al. (2015) |

REFERENCES

Throughout this application, various references describe the state of the art to which this invention pertains. The disclosures of these references are hereby incorporated by reference into the present disclosure.

Angelucci S, Ciavardelli D, Di Giuseppe F, Eleuterio E, Sulpizio M, Tiboni G M, Giampietro F, Palumbo P, Di Ilio C. Proteome analysis of human follicular fluid. *Biochim Biophys Acta* 2006; 1764:1775-85.

Assou S, Haouzi D, Mahmoud K, Aouacheria A, Guillemin Y, Pantesco V, Rème T, Dechaud H, De Vos J, Hamamah S. A non-invasive test for assessing embryo potential by gene expression profiles of human cumulus cells: a proof of concept study. *Mol Hum Reprod* 2008; 14:711-9.

Assou S, Haouzi D, De Vos J, Hamamah S. Human cumulus cells as biomarkers for embryo and pregnancy outcomes. *Mol Hum Reprod* 2010; 16:531-8.

Aydiner F, Yetkin C E, Seli E. Perspectives on emerging biomarkers for non-invasive assessment of embryo viability in assisted reproduction. *Curr Mol Med* 2010; 10:206-15.

Baka S, Malamitsi-Puchner A. Novel follicular fluid factors influencing oocyte developmental potential in IVF: a review. *Reprod Biomed Online* 2006; 12:500-6.

Best C L, Pudney J, Anderson D J, Hill J A. Modulation of human granulosa cell steroid production in vitro by tumor necrosis factor alpha: implications of white blood cells in culture. *Obstet Gynecol* 1994; 84:121-7.

Borowiecka M, Wojsiat J, Polac I, Radwan M, Radwan P, Zbikowska H M. Oxidative stress markers in follicular fluid of women undergoing in vitro fertilization and embryo transfer. *Syst Biol Reprod Med* 2012; 58:301-5.

Chen K, Zhang H, Zhang L N, Ju S Q, Qi J, Huang D F, Li F, Wei Q, Zhang J. Value of circulating cell-free DNA in diagnosis of hepatocelluar carcinoma. *World J Gastroenterol* 2013; 19:3143-9.

Czamanski-Cohen J, Sarid O, Cwikel J, Lunenfeld E, Douvdevani A, Levitas E, Har-Vardi I. Increased plasma cell-free DNA is associated with low pregnancy rates among women undergoing IVF-embryo transfer. *Reprod Biomed Online* 2013; 26:36-41.

Czamanski-Cohen J, Sarid O, Cwikel J, Levitas E, Lunenfeld E, Douvdevani A, Har-Vardi I. Decrease in cell free DNA levels following participation in stress reduction techniques among women undergoing infertility treatment. *Arch Womens Ment Health* 2014.

da Silva Filho B F, Gurgel A P, Neto M Á, de Azevedo D A, de Freitas A C, Silva Neto Jda C, Silva L A. Circulating cell-free DNA in serum as a biomarker of colorectal cancer. *J Clin Pathol* 2013; 66:775-8.

De Placido G, Alviggi C, Clarizia R, Mollo A, Alviggi E, Strina I, Fiore E, Wilding M, Pagano T, Matarese G. Intra-follicular leptin concentration as a predictive factor for in vitro oocyte fertilization in assisted reproductive techniques. *J Endocrinol Invest* 2006; 29:719-26.

Ecker J L, Laufer M R, Hill J A. Measurement of embryotoxic factors is predictive of pregnancy outcome in women with a history of recurrent abortion. *Obstet Gynecol* 1993; 81:84-7.

Estes S J, Ye B, Qiu W, Cramer D, Hornstein M D, Missmer S A. A proteomic analysis of IVF follicular fluid in women <or=32 years old. Fertil Steril 2009; 92:1569-78.

Feng W G, Sui H S, Han Z B, Chang Z L, Zhou P, Liu D J, Bao S, Tan J H. Effects of follicular atresia and size on the developmental competence of bovine oocytes: a study using the wellin-drop culture system. *Theriogenology* 2007; 67:1339-50.

Gahan P B, Anker P, Stroun M. Metabolic DNA as the origin of spontaneously released DNA? *Ann N Y Acad Sci* 2008; 1137:7-17.

Gahan P B. Biology of circulating nucleic acids and possible roles in diagnosis and treatment in diabetes and cancer. *Infect Disord Drug Targets* 2012; 12:360-70.

Gao Y J, He Y J, Yang Z L, Shao H Y, Zuo Y, Bai Y, Chen H, Chen X C, Qin F X, Tan S et al. Increased integrity of circulating cell-free DNA in plasma of patients with acute leukemia. *Clin Chem Lab Med* 2010; 48:1651-6.

Giacona M B, Ruben G C, Iczkowski K A, Roos T B, Porter D M, Sorenson G D. Cell-free DNA in human blood plasma: length measurements in patients with pancreatic cancer and healthy controls. *Pancreas* 1998; 17:89-97.

Guerif F, Le Gouge A, Giraudeau B, Poindron J, Bidault R, Gasnier O, Royere D. Limited value of morphological assessment at days 1 and 2 to predict blastocyst development potential: a prospective study based on 4042 embryos. *Hum Reprod* 2007; 22:1973-81.

Han Z B, Lan G C, Wu Y G, Han D, Feng W G, Wang J Z, Tan J H. Interactive effects of granulosa cell apoptosis, follicle size, cumulus-oocyte complex morphology, and cumulus expansion on the developmental competence of goat oocytes: a study using the well-in-drop culture system. *Reproduction* 2006; 132:749-58.

Hart E A, Patton W C, Jacobson J D, King A, Corselli J, Chan P J. Luteal phase serum cell-free DNA as a marker of failed pregnancy after assisted reproductive technology. *J Assist Reprod Genet* 2005; 22:213-7.

Herrero J, Meseguer M. Selection of high potential embryos using time-lapse imaging: the era of morphokinetics. *Fertil Steril* 2013; 99:1030-4.

Jahr S, Hentze H, Englisch S, Hardt D, Fackelmayer F O, Hesch R D, Knippers R. DNA fragments in the blood plasma of cancer patients: quantitations and evidence for their origin from apoptotic and necrotic cells. *Cancer Res* 2001; 61:1659-65.

Jiang N, Reich C F 3rd, Pisetsky D S. Role of macrophages in the generation of circulating blood nucleosomes from dead and dying cells. *Blood* 2003; 102:2243-50.

Kamat A A, Baldwin M, Urbauer D, Dang D, Han L Y, Godwin A, Karlan B Y, Simpson J L, Gershenson D M, Coleman R L et al. Plasma cell-free DNA in ovarian cancer: an independent prognostic biomarker. *Cancer* 2010; 116:1918-25.

Krisher R L. The effect of oocyte quality on development. *J Anim Sci.* 2004; 82:E14-23.

Lédée N, Gridelet V, Ravet S, Jouan C, Gaspard O, Wenders F, Thonon F, Hincourt N, Dubois M, Foidart J M et al. Impact of follicular G-CSF quantification on subsequent embryo transfer decisions: a proof of concept study. *Hum Reprod* 2013; 28:406-13.

Liao G J, Gronowski A M, Zhao Z. Non-invasive prenatal testing using cell-free fetal DNA in maternal circulation. *Clin Chim Acta* 2014; 428:44-50.

Lin P, Rui R. Effects of follicular size and FSH on granulosa cell apoptosis and atresia in porcine antral follicles. *Mol Reprod Dev* 2010; 77:670-8.

Malizia B A, Wook Y S, Penzias A S, Usheva A. The human ovarian follicular fluid level of interleukin-8 is associated with follicular size and patient age. *Fertil Steril* 2010; 93:537-43.

Mandel P, Metais P. Les acides nucléiques du plasma sanguin chez l'homme. *C R Acad Sci Paris* 1948; 142: 241-243.

Mendoza C, Ruiz-Requena E, Ortega E, Cremades N, Martinez F, Bernabeu R, Greco E, Tesarik J. Follicular fluid markers of oocyte developmental potential. *Hum Reprod* 2002; 17:1017-22.

Mermillod P, Oussaid B, Cognié Y. Aspects of follicular and oocyte maturation that affect the developmental potential of embryos. *J Reprod Fertil Suppl* 1999; 54:449-60.

Meseguer M, Herrero J, Tejera A, Hilligsøe K M, Ramsing N B, Remohí J. The use of morphokinetics as a predictor of embryo implantation. *Hum Reprod* 2011; 26:2658-71.

Montgomery Rice V, Limback S D, Roby K F, Terranova P F. Differential responses of granulosa cells from small and large follicles to follicle stimulating hormone (FSH) during the menstrual cycle and acyclicity: effects of tumour necrosis factor-alpha. *Hum Reprod* 1998; 13:1285-91.

Nandi S, Kumar V G, Manjunatha B M, Gupta P S. Biochemical composition of ovine follicular fluid in relation to follicle size. *Dev Growth Differ* 2007; 49:61-6.

Nishigaki A, Okada H, Okamoto R, Sugiyama S, Miyazaki K, Yasuda K, Kanzaki H. Concentrations of stromal cell-derived factor-1 and vascular endothelial growth factor in relation to the diameter of human follicles. *Fertil Steril* 2011; 95:742-6.

Paci M, Maramotti S, Bellesia E, Formisano D, Albertazzi L, Ricchetti T, Ferrari G, Annessi V, Lasagni D, Carbonelli C et al. Circulating plasma DNA as diagnostic biomarker in nonsmall cell lung cancer. *Lung Cancer* 2009; 64:92-7.

Pearson H. Safer embryo tests could boost IVF pregnancy rates. *Nature* 2006; 444:12-3.

Pisetsky D S, Fairhurst A M. The origin of extracellular DNA during the clearance of dead and dying cells. *Autoimmunity* 2007; 40:281-4.

Revelli A, Delle Piane L, Casano S, Molinari E, Massobrio M, Rinaudo P. Follicular fluid content and oocyte quality:

from single biochemical markers to metabolomics. *Reprod Biol Endocrinol* 2009; 7:40.

Rodgers R J, Irving-Rodgers H F. Formation of the ovarian follicular antrum and follicular fluid. *Biol Reprod* 2010; 82:1021-9.

Rotterdam ESHRE/ASRM-Sponsored PCOS consensus workshop group. Revised 2003 consensus on diagnostic criteria and long-term health risks related to polycystic ovary syndrome (PCOS). *Hum Reprod* 2004; 19:41-7.

Sargent I L, Dokras A. Embryotoxicity as a marker for recurrent pregnancy loss. *Am J Reprod Immunol* 1996; 35:383-7.

Schwarzenbach H, Hoon D S, Pantel K. Cell-free nucleic acids as biomarkers in cancer patients. *Nat Rev Cancer* 2011; 11:426-37.

Schwarzenbach H, Müller V, Milde-Langosch K, Steinbach B, Pantel K. Evaluation of cellfree tumour DNA and RNA in patients with breast cancer and benign breast disease. *Mol Biosyst* 2011; 7:2848-54.

Stigliani S, Anserini P, Venturini P L, Scaruffi P. Mitochondrial DNA content in embryo culture medium is significantly associated with human embryo fragmentation. *Hum Reprod* 2013; 28:2652-60.

Stroun M, Lyautey J, Lederrey C, Olson-Sand A, Anker P. About the possible origin and mechanism of circulating DNA apoptosis and active DNA release. *Clin Chim Acta.* 2001 November; 313(1-2): 139-42.

Sutton M L, Gilchrist R B, Thompson J G. Effects of in-vivo and in-vitro environments on the metabolism of the cumulus-oocyte complex and its influence on oocyte developmental capacity. *Hum Reprod Update* 2003; 9:35-48.

Swarup V, Rajeswari M R. Circulating (cell-free) nucleic acids—a promising, non-invasive tool for early detection of several human diseases. *FEBS Lett* 2007; 581:795-9.

Umetani N, Kim J, Hiramatsu S, Reber H A, Hines O J, Bilchik A J, Hoon D S. Increased integrity of free circulating DNA in sera of patients with colorectal or periampullary cancer: direct quantitative PCR for ALU repeats. *Clin Chem* 2006; 52:1062-9.

Uyar A, Torrealday S, Seli E. Cumulus and granulosa cell markers of oocyte and embryo quality. *Fertil Steril* 2013; 99:979-97.

van Montfoort A P, Geraedts J P, Dumoulin J C, Stassen A P, Evers J L, Ayoubi T A. Differential gene expression in cumulus cells as a prognostic indicator of embryo viability: a microarray analysis. *Mol Hum Reprod* 2008; 14:157-68.

Vlassov V V, Laktionov P P, Rykova E Y. Circulating nucleic acids as a potential source for cancer biomarkers. *Curr Mol Med* 2010; 10:142-65.

Wen X, Tozer A J, Butler S A, Bell C M, Docherty S M, Iles R K. Follicular fluid levels of inhibin A, inhibin B, and activin A level reflect changes in follicle size but are not independent markers of the oocyte's ability to fertilize. *Fertil Steril* 2006; 85:1723-9.

Wright C F, Burton H. The use of cell-free fetal nucleic acids in maternal blood for noninvasive prenatal diagnosis. *Hum Reprod Update* 2009; 15:139-51.

Yanaihara A, Mitsukawa K, Iwasaki S, Otsuki K, Kawamura T, Okai T. High concentrations of lactoferrin in the follicular fluid correlate with embryo quality during in vitro fertilization cycles. *Fertil Steril* 2007; 87:279-82.

Yang M Y, Rajamahendran R. Morphological and biochemical identification of apoptosis in small, medium, and large bovine follicles and the effects of follicle-stimulating hormone and insulin-like growth factor-I on spontaneous apoptosis in cultured bovine granulosa cells. *Biol Reprod* 2000; 62:1209-17.

The invention claimed is:

1. An in vitro non-invasive method for determining the quality of an embryo comprising the steps of i) extracting cell free nucleic acids and miRNAs from a follicular fluid sample obtained from an individual pre-ovulatory follicle in the embryo, ii) measuring, in extracted cell free nucleic acids and miRNAs, a level of cell free nucleic acids and/or a level of at least one miRNA selected from the group consisting of let7-b and miR-29a, iii) comparing the level of cell free nucleic acids, the level of let7-B miRNA and/or the level of miR-29a miRNA measured at step ii) with a corresponding reference value, wherein the corresponding reference value is derived from a level of cell free nucleic acids, let7-B miRNA, and/or miR-29a obtained from a competent embryo, and iv) determining that the embryo is competent when the level of cell free nucleic acids measured at step ii) is lower than the corresponding reference value, the level of let7-b measured at step ii) is lower than the corresponding reference value, and/or the level of miR-29a measured at step ii) is higher than the corresponding reference value.

2. A method for enhancing a pregnancy outcome of a patient comprising i) extracting cell free nucleic acids and miRNAs from a follicular fluid sample obtained from individual pre-ovulatory follicles in a plurality of embryos of said patient, ii) measuring a level of cell free nucleic acids and/or a level of at least one miRNA selected from the group consisting of let7-b and miR-29a, iii) comparing the level of cell free nucleic acids, the level of let7-B miRNA and/or the level of miR-29a miRNA measured at step ii) with a corresponding reference value, wherein the corresponding reference value is derived from a level of cell free nucleic acids, let7-B miRNA, and/or miR-29a obtained from a competent embryo, and iv) determining that the embryo is competent when the level of cell free nucleic acids measured at step ii) is lower than the corresponding reference value, the level of let7-b measured at step ii) is lower than the corresponding reference value, and/or the level of miR-29a measured at step ii) is higher than the corresponding reference value, v) selecting an embryo determined to be competent in step iv, and vi) implanting the competent embryo selected at step v) in the uterus of said patient.

3. The method of claim 1, wherein the level of miR29a is measured in step ii).

4. The method of claim 1, wherein the level of cell free nucleic acids is measured in step ii).

5. The method of claim 1, wherein the levels of cell free nucleic acids, let7-b, and miR-29a are measured in step ii).

6. The method of claim 2, wherein the level of miR29a is measured in step ii).

7. The method of claim 2, wherein the levels of cell free nucleic acids, let7-b, and miR-29a are measured in step ii).

* * * * *